United States Patent
Bereznak et al.

[11] Patent Number: 6,166,208
[45] Date of Patent: Dec. 26, 2000

[54] PREPARATION OF FUNGICIDAL QUINAZOLINONES AND USEFUL INTERMEDIATES

[75] Inventors: James Francis Bereznak, Aston, Pa.; Eric Allen Marshall, Elkton, Md.; Charlene Gross Sternberg; Jeffrey Arthur Sternberg, both of Wilmington, Del.; King-Mo Sun, Hockessin, Del.

[73] Assignee: E. I. du Pont de Nemours and Company, Wilmington, Del.

[21] Appl. No.: 09/202,394

[22] PCT Filed: Jun. 12, 1997

[86] PCT No.: PCT/US97/10254

§ 371 Date: Dec. 9, 1998

§ 102(e) Date: Dec. 9, 1998

[87] PCT Pub. No.: WO97/48684

PCT Pub. Date: Dec. 24, 1997

Related U.S. Application Data

[60] Provisional application No. 60/020,423, Jun. 18, 1996.

[51] Int. Cl.[7] .................. C07D 239/96; C07C 271/68
[52] U.S. Cl. ............................................. 544/285
[58] Field of Search .......................... 544/285

[56] References Cited

U.S. PATENT DOCUMENTS

| | | |
|---|---|---|
| 3,755,582 | 8/1973 | Bullock .................................. 424/251 |
| 3,867,384 | 2/1975 | Bullock et al. ....................... 260/256.4 |

FOREIGN PATENT DOCUMENTS

| | | |
|---|---|---|
| 712 849 | 5/1996 | European Pat. Off. . |
| 1 038 729 | 6/1965 | United Kingdom . |
| WO 94/26722 | 11/1994 | WIPO . |
| WO 98/40363 | 9/1998 | WIPO . |

OTHER PUBLICATIONS

William D. Dean et al., Synthesis of 4(3H)–Quinazolinones from Derivatives of Methyl–2–Isothiocyanatobenzoate, *J. Heterocyclic Chem.*, 19, 1117–1123, Sep.–Oct. 1982.
*Chemical Abstracts*, 107, No. 25, Abstract No. 228515k, re. R. Lakhan, et al., Studies of 4(3H)Quinazolinone Derivatives, 1987.
*Chemical Abstracts*, 89, No. 13, Abstract No. 109345e re. P. Bhargava et al., Synthesis of 6,8–Diiodo–S–Substit.2Thio–3–Aryl(alkyl)–4(3H)–quinazolinones,, 1978.
Urleb et al., The Synthesis and Transformation of 2–Ethoxycarbonyl–3–IsothiocyanaTopyridine, Pyrido[3, 2–d]pyrimidines and some Azolopyridol[3,2–d]pyrimidines, *J. Heterocycl. Chem.* (27) 407 (1990).
E.P. Papadopoulos et al, Convenient Preparation of N–Substituted 2–Amino–4H–3,1–benzoxazin–4–Ones and 3–Substituted 2,4(1H,3H)–Quinazolinediones,, *J. Heterocycl. Chem.*, (19) 269 (1982).

*Primary Examiner*—Richard L. Raymond
*Assistant Examiner*—Hong Liu

[57] ABSTRACT

This invention provides advantageous processes for preparing quinazolinones of Formula I

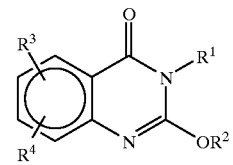

I wherein:
$R^1$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; or $C_3$–$C_{10}$ alkynyl;
$R^2$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; $C_4$–$C_{10}$ cycloalkyl; $C_4$–$C_{10}$ halocycloalkyl; or $C_3$–$C_{10}$ alkynyl; and
$R^3$ and $R^4$ are each independently hydrogen or halogen; from compounds containing the moiety IIg

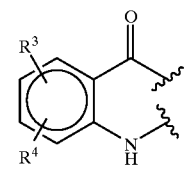

IIg This invention further provides certain compounds of Formula II, IIIa, or IVa

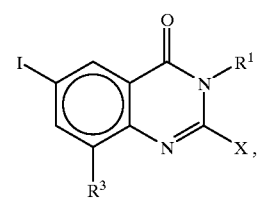

II

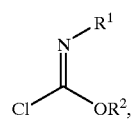

IIIa

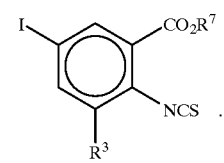

IVa where $R^7$ is $C_2$–$C_6$ alkyl.

12 Claims, No Drawings

PREPARATION OF FUNGICIDAL QUINAZOLINONES AND USEFUL INTERMEDIATES

This application is a national filing under 35 $USC_{371}$ of International Application No. PCT/US97/10254 filed Jun. 12, 1997 and claims the priority benefit of U.S. Provisional Application Ser. No. 60/020,423 filed Jun. 18, 1996.

FIELD OF THE INVENTION

This invention relates to compounds and processes for the preparation of fungicidal quinazolinones.

BACKGROUND OF THE INVENTION

WO 94/26722 generically discloses conversion of anthranilic acids to 2-thioquinazolinediones with isothiocyanates (see also: U.S. Pat. No. 3,755,582). WO 94/26722 discloses that the reaction is preferably performed in the presence of a base such as triethylamine.

WO 94/26722 also discloses conversion of 2-thioquinazolinediones to 2-chloro-4(3H)-quinzolinones using sulfuryl chloride (see also: U.S. Pat. No. 3,867,384). No mention is made of using phosgene for this transformation.

WO 94/26722 and U.S. Pat. No. 3,755,582 generically disclose 2-alkylthio-quinazolinones.

WO 94/26722 generically discloses the condensation of anthranilic acid esters with thiophosgene to form isothiocyanate esters. Similar procedures are disclosed in *J. Herterocycl. Chem.*, (1990), 27, 407.

The preparation of 2,4-(1H,3H)-quinazolinediones from anthranilic acid and esters plus isocyanates is cited in *J. Heterocycl. Chem.*, (1982), 19, 269.

EP-A-712849 discloses a process for the preparation of quinazoline-2,4-diones.

SUMMARY OF THE INVENTION

This invention provides advantageous processes for preparing quinazolinones of Formula I

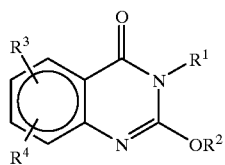

I wherein:

$R^1$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; or $C_3$–$C_{10}$ alkynyl;

$R^2$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; $C_4$–$C_{10}$ cycloalkyl; $C_4$–$C_{10}$ halocycloalkyl; or $C_3$–$C_{10}$ alkynyl; and $R^3$ and $R^4$ are each independently hydrogen or halogen; from compounds containing the moiety IIg

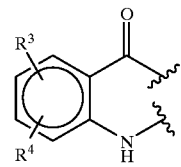

IIg

The quinazolinones of Formula I are useful as fungicides and/or intermediates for preparing fungicides. The processes for preparing the quinazolinones of Formula I provided herein are characterized by employing a process sequence (A-E) as described below.

Process A

One process for preparing compounds of Formula I is provided which comprises (a) treating a 2-thioquinazolinedione of Formula IIa

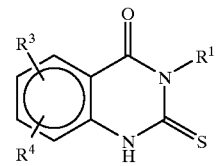

IIa with phosgene in an inert solvent, at a temperature from about 50 to 120° C., and a pressure of from about 1 to 5 atmospheres ($1.013 \times 10^5$ to $5.065 \times 10^5$ Pa), to form a 2-chloro-4(3H)-quinazolinone of Formula IIb

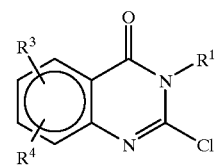

IIb and (b) treating the 2-chloro-4(3H)-quinazolinone with a metal alkoxide of Formula $M^+$ ($^-OR^2$) wherein M is lithium, sodium or potassium, in an inert solvent, at a temperature of from about −20 to 50° C., and a pressure of from about 1 to 5 atmospheres ($1.013 \times 10^5$ to $5.065 \times 10^5$ Pa).

Process B

Another process for preparing compounds of Formula I is provided which comprises treating a quinazolinedione of Formula IIc

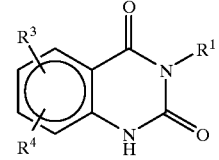

IIc with an alkylating agent of the formula $R^2$—Z where Z is iodide, bromide, chloride, alkyl sulfonate, aryl sulfonate, sulfate, or oxonium tetrafluoroborate in an inert solvent at a temperature of from about 25 to 110° C. and a pressure of from about 1 to 5 atmospheres ($1.013 \times 10^5$ to $5.065 \times 10^5$ Pa).

The quinazolinedione of Formula IIc may be prepared by (a1) contacting an isatoic anhydride of Formula 2

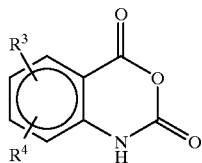

2 with a primary amine of the formula $R^1$—$NH_2$ to form the aminobenzamide of Formula 3

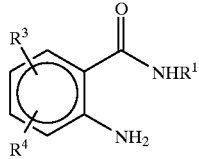

3 and (b1) treating the aminobenzamide of Formula 3 with phosgene in an inert solvent at a temperature of from about 20 to 120° C. and a pressure of from about 1 to 5 atmospheres ($1.013 \times 10^5$ to $5.065 \times 10^5$ Pa) to form the quinazolinedione of Formula IIc, or by (a2) reacting a compound of Formula 1b

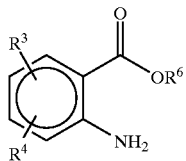

1b wherein $R^6$ is hydrogen or $C_1$–$C_6$ alkyl with an isocyanate of the formula $R^1$—N=C=O in a suitable solvent and (b2) distilling the solvent and heating the neat residue at temperatures ranging from about 150 to 250° C. and a pressure of from about 1 to 5 atmospheres ($1.013 \times 10^5$ to $5.065 \times 10^5$ Pa) for about 0.25 to 24 h to form the quinazolinedione of Formula IIc, or by (a3) contacting an isotoic anhydride of Formula 2 with a symmetrical N,N'-dialkylurea of formula $R^1NHC(O)NHR^1$ to form the quinazolinedione of Formula IIc.

Process C

Another process for preparing compounds of Formula I is provided which comprises (a) contacting a 2-thioquinazolinedione of Formula IIa

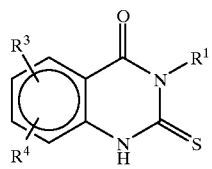

IIa with an alkylating agent of the formula $R^5$—Z wherein $R^5$ is $C_1$–$C_6$ alkyl in an inert solvent at a temperature of from about −10 to 60° C. and a pressure of from about 1 to 5 atmospheres ($1.013 \times 10^5$ to $5.065 \times 10^5$ Pa) to form a 2-alkylthio-4(3H)-quinazolinone of Formula IId

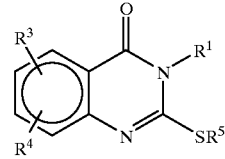

IId and (b) treating the 2-alkylthio-4(3H)-quinazolinone of Formula IId with a metal alkoxide of the formula $M^+(^-OR^2)$ wherein M is lithium, sodium or potassium in an inert solvent at a temperature of from about −30 to 50° C. and a pressure of from about 1 to 5 atmospheres ($1.013 \times 10^5$ to $5.065 \times 10^5$ Pa).

Process D

Another process for preparing compounds of Formula I is provided which comprises treating an anthranilic acid or ester of Formula 1b

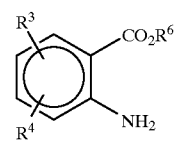

1b wherein $R^6$ is hydrogen or $C_1$–$C_6$ alkyl with a compound of Formula III

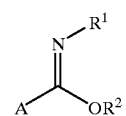

III wherein A is Cl or S($C_1$–$C_6$ alkyl) optionally in the presence of an acid or a base, and an inert solvent at a temperature of from about 0 to 100° C., and a pressure of from about 1 to 5 atmospheres ($1.013 \times 10^5$ to $5.065 \times 10^5$ Pa).

Process E

Another process for preparing compounds of Formula I is provided which comprises (a) treating an anthranilate ester of Formula 1c

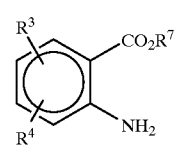

1c wherein $R^7$ is $C_1$–$C_6$ alkyl with thiophosgene or carbon disulfide in an inert solvent at temperature of from about 25 to 100° C. and a pressure of from about 1 to 5 atmospheres ($1.013 \times 10^5$ to $5.065 \times 10^5$ Pa) to form the isothiocyanate ester of Formula IV

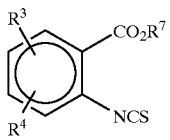

IV (b) treating the isothiocyanate ester with an alcohol of the formula $R^2OH$ in an inert solvent at a temperature of from about 25 to 150° C. and a pressure from about 1 to 5 atmospheres ($1.013 \times 10^5$ to $5.065 \times 10^5$ Pa) to form the thionocarbamate of Formula 4

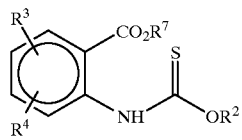

4 and (c) treating the thionocarbamate of Formula 4 with an amine of the formula $R^1$—$NH_2$ in an inert solvent, at a temperature of from about 25 to 200° C., and a pressure of from about 1 to 5 atmospheres ($1.013 \times 10^5$ to $5.065 \times 10^5$ Pa).

This invention further provides a compound of Formula II

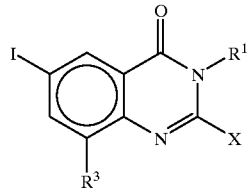

II wherein:

$R^1$ is $C_1$–$C_{10}$ alkyl, $C_3$–$C_{10}$ alkenyl, $C_4$–$C_{10}$ cycloalkylalkyl or $C_3$–$C_{10}$ alkynyl; $R^3$ is H or I; and X is OH, SH, or Cl.

This invention further provides a compound of Formula IIIa

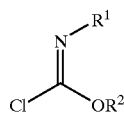

IIIa wherein $R^1$ and $R^2$ are $C_3$ alkyl.

This invention further provides a compound of Formula IVa

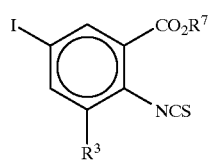

IVa wherein $R^3$ is H or I and $R^7$ is $C_2$–$C_6$ alkyl.

DETAILED DESCRIPTION OF THE INVENTION

Compounds of this invention can exist as one or more stereoisomer. The various stereoisomers include enantiomers, diastereomers and geometric isomers. One skilled in the art will appreciate that one stereoisomer may be more desirable and how to separate said stereoisomers. Accordingly, the present invention comprises mixtures, individual stereoisomers, and optically active mixtures of compounds of Formulae I, II and IVa.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl, hexyl, heptyl, octyl, nonyl, or decyl isomers. The term "1–2 alkyl" indicates that one or two of the available positions for that substituent may be alkyl which are independently selected. "Alkenyl" includes straight-chain or branched alkenes such as vinyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Cycloalkyl" includes, for example, cyclopropyl, cyclobutyl, cyclopentyl, and cyclohexyl.

Examples of "cycloalkylalkyl" include cyclopropylmethyl, cyclopentylethyl, and other cycloalkyl moieties bonded to straight-chain or branched alkyl groups.

The term "halogen" includes fluorine, chlorine, bromine or iodine.

The total number of carbon atoms in a substituent group is indicated by the "$C_i$–$C_j$" prefix where i and j are numbers from 1 to 10. For example, $C_1$–$C_3$ alkyl designates methyl through propyl; and $C_4$ alkyl designates the various isomers of an alkyl group containing a total of four carbon atoms.

When a group contains a substituent which can be hydrogen, for example $R^3$ or $R^4$, then, when this substituent is taken as hydrogen, it is recognized that this is equivalent to said group being unsubstituted.

Compounds of this invention may also exist as a mixture of tautomers. For example, a compound of Formula IIa may exist in one or both of the tautomeric forms illustrated below.

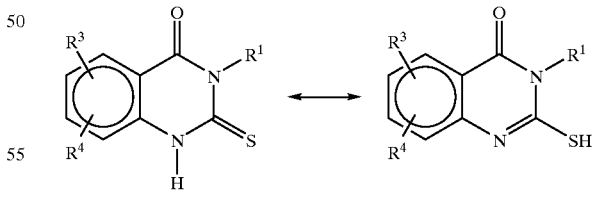

IIa          IIa

One skilled in the art will appreciate that one tautomer may predominate over the other. The present invention comprises both tautomeric forms as well as mixtures thereof of compounds of Formulae IIa and IIc.

The processes of the present invention and methods for the preparation of compounds of Formula I, Formula II (see Schemes 1, 2, and 5), Formula IIIa (see Scheme 16), and Formula IVa (see Scheme 18) are described below. One skilled in the art will recognize when the order of addition of reagents is important in the processes of this invention.

Of note are processes wherein $R^1$ is $C_1$–$C_{10}$ alkyl, $C_3$–$C_{10}$ alkenyl, $C_4$–$C_{10}$ cycloalkylalkyl, $C_4$–$C_{10}$ halocycloalkylalkyl, or $C_3$–$C_{10}$ alkynyl; and $R^2$ is $C_1$–$C_{10}$ alkyl, $C_3$–$C_{10}$ alkenyl, $C_4$–$C_{10}$ cycloalkylalkyl or $C_3$–$C_{10}$ alkynyl. Preferred processes include processes (A-E) to prepare compounds of Formula I wherein $R^1$ is $C_1$–$C_3$ alkyl, $R^2$ is $C_1$–$C_3$ alkyl, $R^3$ is Br or I, and $R^4$ is H, Br or I.

Process A—beginning with anthranilates of Formula I a or aminobenzamides of Formula 3

Compounds of Formula I can be prepared by Process A illustrated in Schemes 1–3. The 2-thioquinazolinedione of Formula IIa may be prepared by condensing an anthranilic acid (2-aminobenzoic acid) of Formula 1a with an isothiocyanate of Formula 5 in the presence of a base as illustrated in Scheme 1.

Scheme 1

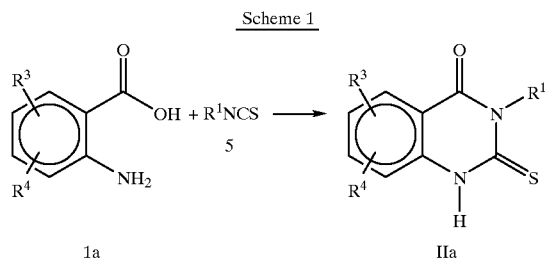

Only one equivalent of the isothiocyanate is required; however, excess reagent can be used. The reaction is run in a solvent such as dimethylacetamide, cyclohexane, hexane, methanol, ethanol, n-propanol, i-propanol, chloroform, 1,2-dichloroethane, N,N-dimethylformamide, ethyl acetate, n-propyl acetate, i-propyl acetate, diethoxymethane, tetrahydrofuran, dioxane, toluene, water or xylene. Alcohol, ester and aromatic solvents such as ethanol, propanol, n-propyl acetate and xylene are preferred. The reaction temperature is from about 60 to 150° C. The preferred temperature range is from about 75 to 145° C.

The base accelerates the reaction and improves the solubility of the anthranilic acid in the solvent. One equivalent of base is generally used. Use of less than one equivalent leads to longer reaction times. Greater than one equivalent offers no advantage. Suitable bases include trialkylamine bases such as trimethylamine, triethylamine, tripropylamine, tributylamine and N,N-diisopropylethylamine, as well as inorganic bases such as sodium hydroxide and potassium hydroxide.

The reaction is conducted by combining the base, isothiocyanate, and anthranilic acid in a solvent and heating at atmospheric pressure. If desired, the isothiocyanate can be prepared directly in the reaction vessel prior to the addition of the anthranilic acid. The isothiocyanate can be isolated and purified prior to use but it is not necessary. For example, the isothiocyanate can be prepared by combining carbon disulfide, a metal hydroxide such as potassium hydroxide, and a primary amine, and heating at 30–100° C. for 30 min to 2 h. Water is one of many suitable solvents for this reaction. An alkyl chloroformate is then added. The resulting isothiocyanate can be isolated by phase separation or distillation, or combined directly with a base and an anthranilic acid as described above to give the 2-thioquinazolinedione. Alternatively, the isothiocyanate can be added to the hot reaction mixture, or the reaction can be run in a sealed vessel at a pressure of about 1 to 5 atmospheres ($1.013 \times 10^5$ to $5.065 \times 10^5$ Pa). If desired a water-immiscible solvent is used, the water generated in the reaction can be removed using a Dean-Stark trap. The 2-thioquinazolinedione precipitates from the reaction mixture as it forms. After heating for about 1 to 48 h, the reaction mixture is cooled and filtered. The product is dried, or the wetcake can be used directly in the next step if the solvent is compatible with the reaction conditions in the following step.

Alternatively, 2-thioquinazolinediones of Formula IIa can be prepared by reacting aminobenzamides of Formula 3 with carbon disulfide as depicted in Scheme 1a.

Scheme 1a

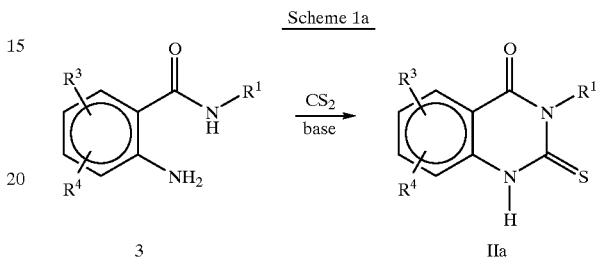

Similar transformations are known in the art (Mizuno, et. al., Chemistry Express, (1991), 6, 439). The reaction may be conducted using a variety of solvents and bases. Suitable solvents for this transformation include (but are not limited to) methanol, ethanol, i-propanol, chloroform, 1,2-dichloroethane, N,N-dimethylformamide, N,N-dimethylacetamide, ethyl acetate, n-propyl acetate, i-propyl acetate, diethoxymethane, tetrahydrofuran, dioxane, toluene, xylene, hexanes, and cyclohexanes. Suitable bases for this transformation include (but are not limited to) 1,8-diazabicyclo[5.4.0]undec-7-ene (DBU), 1,4-diazabicyclo[2.2.2]octane (DABCO), 1,5-diazabicyclo[4.3.0]non-5-ene (DBN), trimethylamine, triethylamine, tripropylamine, tributylamine, N,N-diisopropylamine, 4-dimethylaminopyridine, sodium hydroxide, potassium hydroxide, sodium carbonate, and potassium carbonate. Effective amounts of base can range from 0.5–5.0 molar equivalents with respect to aminobenzamide 3. Although reaction concentrations from about 0.2M–2.0M (with respect to aminobenzamide 3) may be employed in conjunction with 1.0–20 molar equivalents of carbon disulfide (with respect to aminobenzamide 3), conditions favoring greater reaction concentration and fewer molar equivalents of carbon disulfide are preferred. The reaction may be conducted at temperatures from about 40° C–200° C. for about 0.5 h–24 h, and workup is achievable by acidification and filtration of the reaction mixture to obtain precipitated IIa.

Aminobenzamides of Formula 3 are accessible from isatoic anhydrides of Formula 2 through contact with amines of Formula 6 (Scheme 2).

Scheme 2

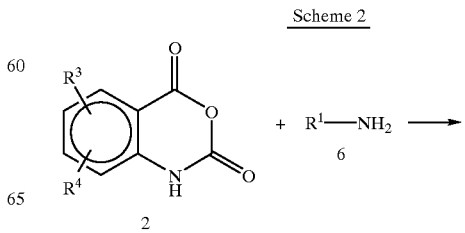

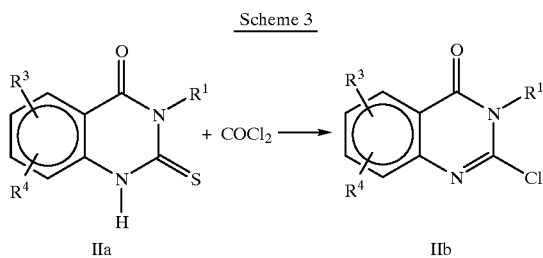

Methods for the preparation of isatoic anhydrides are well-known in the literature. G. M. Coppola in *Synthesis,* (1980), 505 reviews their preparation and discusses their conversion to aminobenzamides (also see Staiger and Wagner in *J. Org. Chem.,* (1953), 18, 1427).

Process A further involves treatment of the 2-thioquinazolinedione of Formula IIa with phosgene in an inert solvent to give the 2-chloro-4(3H)-quinazolinone of Formula IIb (Scheme 3).

Scheme 3

Only one equivalent of phosgene is required, however excess reagent can be used. In addition, a catalyst such as dimethylformamide or dimethyl acetamide may be employed. The reaction is run in an inert solvent such as 1,2-dichloroethane, ethyl acetate, n-propyl acetate, i-propyl acetate, acetonitrile, toluene, xylene or dioxane. Ester solvents such as n-propyl acetate and aromatic solvents such as xylene are preferred. The reaction mixture is heated at about 50 to 120° C. for 15 minutes to 6 h or until the 2-thioquinazolinedione is consumed. The preferred temperature is from about 75 to 115° C.

The reaction is conducted by combining the 2-thioquinazolinedione and the solvent and heating. The phosgene is then introduced. Alternatively, the phosgene can be added at room temperature and the reaction mixture is then heated. The reaction can also be run under pressure with a relief valve to vent the carbonyl sulfide and hydrogen chloride generated as by-products. The 2-chloro-4(3H)-quinazolinone is isolated by evaporation of the solvent and is generally of sufficient purity to be used directly in the next step. Alternatively, the solution or slurry of product can be used directly in the next step with or without first removing the excess phosgene by distillation or sparging with an inert gas such as nitrogen.

The final step in Process A is treatment of the 2-chloro-4(3H)-quinazolinone of Formula IIb with a metal alkoxide of Formula $M^+(^-OR^2)$, wherein M is lithium, sodium or potassium, in an inert solvent to give the quinazolinone of Formula I (Scheme 4).

Scheme 4

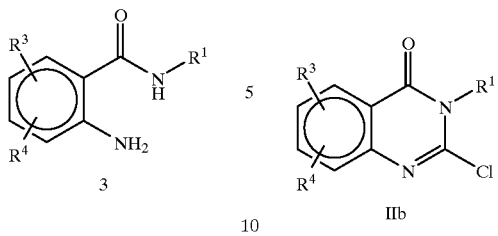

The metal alkoxide is generated by treatment of the alcohol of Formula $R^2OH$ with a base such as sodium or potassium metal, or sodium or potassium hydride. The alkoxide can also be generated in situ from the alcohol and lithium, sodium, or potassium hydroxide with or without removal of the water by distillation. In general, the metal alkoxide is generated in the alcohol solvent and used as a solution. Whether the metal alkoxide is preformed or generated in situ, preferably M is sodium or potassium and $R^2$ is propyl. Preferred reagents include sodium propoxide and potassium propoxide. Only one equivalent of the metal alkoxide is required for the reaction, however excess reagent can be used.

Various solvents can be used for the displacement reaction including methanol, ethanol, n-propanol, i-propanol, methylene chloride, 1,2-dichloroethane, N,N-dimethylformamide, ethyl acetate, n-propyl acetate, i-propyl acetate, diethoxymethane, dimethoxy-ethane, tetrahydrofuran, dioxane, acetone, methyl ethyl ketone, toluene, or xylene. If an ester or alcohol solvent is used, it is desirable to match the alkoxide with the ester group or alcohol to avoid the formation of a mixture of products. Ester solvents such as n-propyl acetate and aromatic solvents such as xylene are preferred.

The reaction is run by adding the metal alkoxide to the 2-chloro-4(3H)-quinazolinone in a solvent at a temperature from about −30 to 50° C. Alternatively, the 2-chloro-4(3H)-quinazolinone can be added to a solution of the metal alkoxide. The preferred reaction temperature is from about −10 to 25° C. The reaction mixture is agitated for 5 minutes to 6 hours or until the 2-chloro-4(3H)-quinazolinone is consumed. If desired, the reaction can also be run under 1 to 5 atmospheres of pressure. After the reaction is complete, the metal chloride salt is removed by washing with water, and the solvent is evaporated to afford the compound of Formula I.

Process B—beginning with Compounds of Formula 2 or 1b

Compounds of Formula I can also be prepared by Process B illustrated in Schemes 2, 5 and 6. As indicated above, an isatoic anhydride of Formula 2 may be contacted with a primary amine of Formula 6 to form the aminobenzamide of Formula 3 (see Scheme 2). Treatment of the aminobenzamide with phosgene affords the 2,4-(1H,3H)-quinazolinedione of Formula IIc (Scheme 5).

Scheme 5

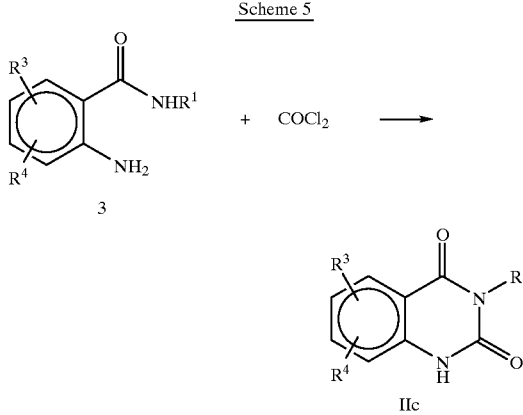

IIc

Only one equivalent of phosgene is required, however excess reagent has no adverse effect on the reaction. The reaction is run in a solvent such as ethyl acetate, propyl acetate, tetrahydrofuran, dioxane, toluene, or xylene. Dioxane is preferred. The temperature for the reaction is from about 20 to 120° C. The preferred temperature range is 75 to 1 10° C. After the reaction is complete, the product can be isolated by cooling and filtration, or by dilution with water and filtering if a water-miscible solvent is used. If the quinazolinedione of Formula IIc is not a solid at room temperature, it can be isolated from the reaction mixture by evaporation of the solvent.

As illustrated in Scheme 6, the 2,4-(1H,3H)-quinazolinedione of Formula IIc is converted to the 4(3H)-quinazolinone of Formula I by treatment with an alkylating agent ($R^2$—Z) such as an $R^2$-iodide, -bromide, -chloride, -alkyl sulfonate [$R^2OS(O)_2(C_1$–$C_3$ alkyl)], -aryl sulfonate [$R^2OS(O)_2$(tolyl) or $R^2OS(O)_2$(phenyl)], sulfate ($R^2OS(O)_2OR^2$), or oxonium tetrafluoroborate [$(R^2)_3OBF_4$].

Scheme 6

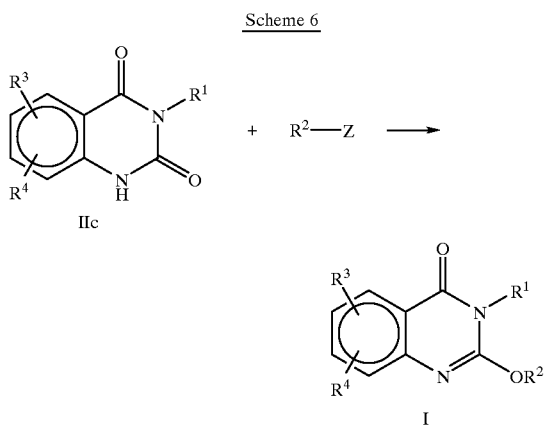

Alkylating agents known to give primarily O— vs. N-alkylation are preferred such as dialkyl sulfates and trialkyloxonium tetrafluoroborates. In all cases other than the trialkyloxonium tetrafluoroborates, a base is added to the reaction. Potassium bases such as potassium hydride, potassium carbonate, and potassium hydroxide are preferred. The reaction is run in an inert solvent such as tetrahydrofuran or methylene chloride at a temperature from about 25 to 110° C. Alternatively, 2,4-(1H,3H)-quinazolinediones of Formula IIc can be prepared by contacting and heating an isotoic anhydride of Formula 2 with a symmetrical N,N'-dialkylurea of formula $R^1NHC(O)NHR^1$ in amide solvents like dimethylacetamide (Scheme 2a).

Scheme 2a

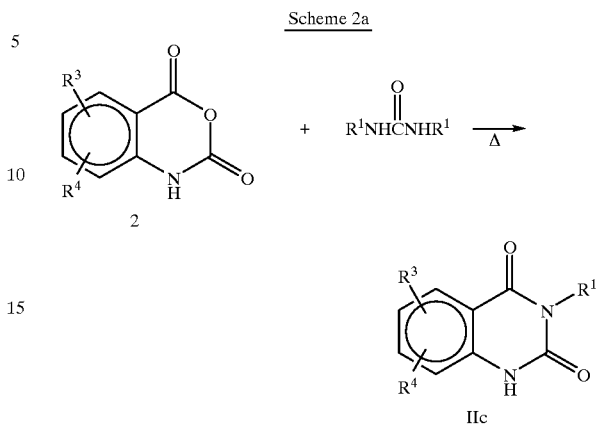

IIc

Alternatively, 2,4-(1H,3H)-quinazolinediones of Formula IIc can be prepared by methods utilizing acid or ester intermediates of the Formula 8 (Scheme 7). Compounds of Formula 8 may be synthesized by reaction of a suitable anthranilic acid or ester of Formula 1b with isocyanates of Formula 7. The starting anthranilic acids and esters of Formula 1b and isocyanates of Formula 7 are well-documented in the literature and are easily accessed by one skilled in the art. The reaction of the materials of Formula 1b and 7 can be conducted in a variety of solvents such as ethanol, petroleum ether, acetonitrile, -N,N-dimethylformamide, dimethylsulfoxide, and tetrahydrofuran, in the presence of a basic catalyst at temperatures ranging from ambient to 200° C. for about 0.5 to 96 h. Examples of similar transformations can be found in *J. Org. Chem.*, (1961) 26, 5238.

Scheme 7

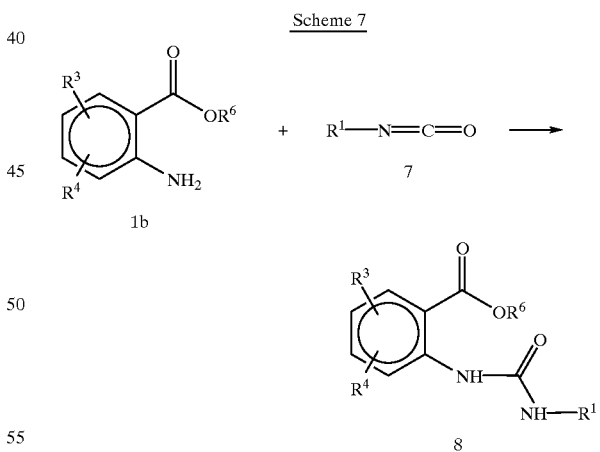

Alternatively, acids of Formula 8a (compounds of Formula 8 wherein $R^6$=H) can be prepared by reacting anhydrides of Formula 2 with an amine of Formula 6 as described in *J. Org. Chem.*, (1953) 18,1427 (Scheme 8). The isatoic anhydrides of Formula 2 are accessible using any of the known means described in the art (e.g.—*J. Org. Chem.*, (1976) 11, 2070). The reaction may be carried out in water, aqueous ethanol, or ethylene glycol at temperatures ranging from about ambient to 150° C. for 0.25 to 24 h. Purification and separation can be achieved by diluting the reaction mixture with water, acidifying, and filtering to provide compounds of Formula 8a.

Scheme 8

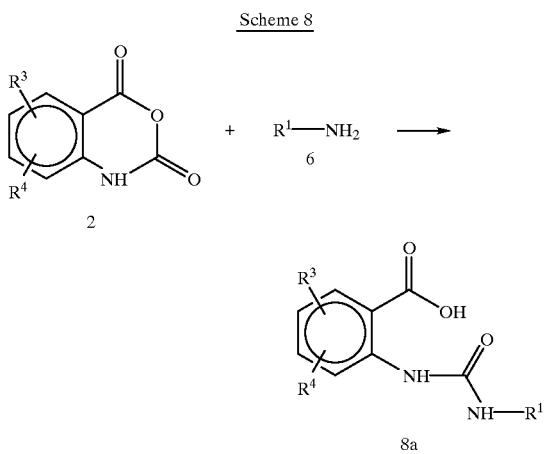

Conversion of compounds of Formula 8 to materials of Formula IIc can be accomplished by heating compounds of Formula 8 either neat or in a suitable solvent at temperatures ranging from about 30 to 220° C. for about 0.25 to 24 h optionally in the presence of an acid or base (Scheme 9). Examples of suitable solvents include ethanol, water, N,N-dimethylformamide, acetonitrile, dimethylsulfoxide, dimethylacetamide, tetrahydrofuran, dioxane. Examples of optional acids include aqueous HCl or $H_2SO_4$. Examples of optional bases include sodium hydroxide or triethylamine. For examples of similar cyclizations, see *J. Org. Chem.*, (1961) 26, 5238, *J. Heterocyclic Chem.*, (1982) 19, 269 and *J. Org. Chem.*, (1953) 18,1427. The isolated products may be obtained by cooling and filtration from the reaction medium, or by concentration and/or trituration with an alcoholic solvent.

Scheme 9

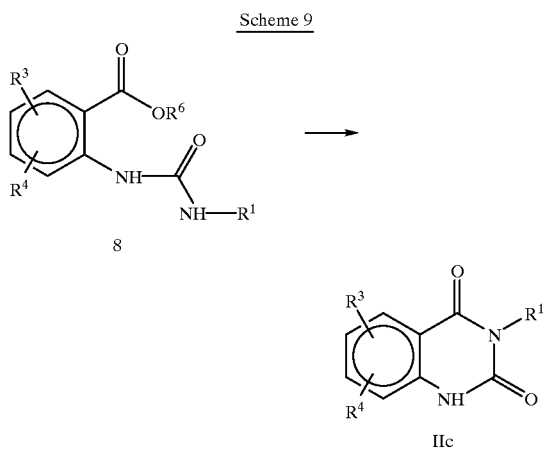

A preferred, single-vessel method for preparing compounds of Formula IIc comprises reacting compounds of Formula 1b with isocyanates of Formula 7 in a suitable solvent as described in Scheme 10, followed by distillation of the solvent and heating of the neat residue at temperatures ranging from about 150 to 250° C. for about 0.25 to 24 h. Trituration of the cooled reaction mass with alcohol and/or ether solvents delivers the purified material of Formula IIc.

Scheme 10

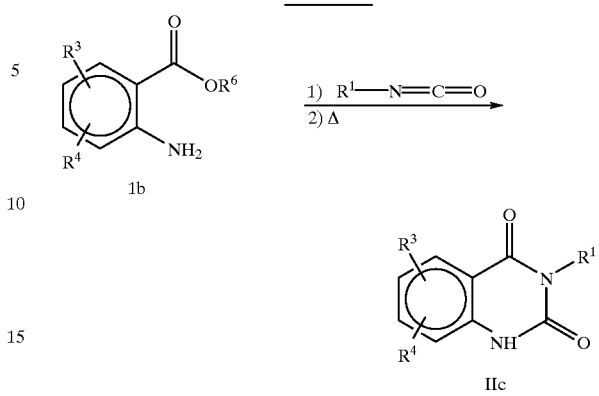

Process C—beginning with Compounds of Formula IIa
Compounds of Formula I can also be prepared by Process C illustrated in Schemes 11 and 12

Scheme 11

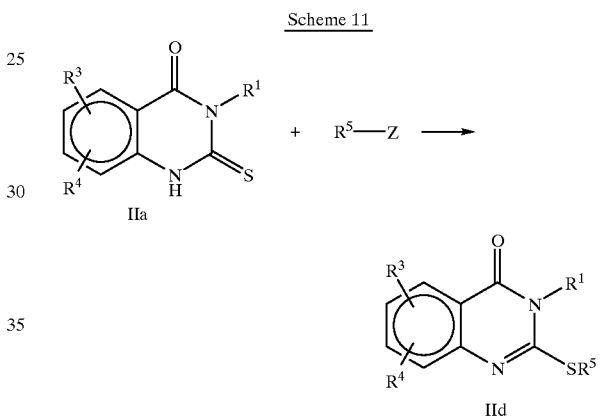

A 2-thioquinazolinedione of Formula IIa described in Process A above is contacted with an alkylating agent to form the 2-alkylthio-4(3H)-quinazolinone of Formula IId (Scheme 11). Suitable alkylating agents ($R^5$-Z) include alkyl iodides [($C_1$–$C_6$ alkyl)-I], alkyl bromides [($C_1$–$C_6$ alkyl)-Br], alkyl chlorides [($C_1$–$C_6$ alkyl)-Cl], dialkyl sulfates [($C_1$–$C_6$ alkyl)$_2$SO$_4$], and alkyl sulphonates [($C_1$–$C_6$ alkyl)OS(O)$_2$CH$_3$, ($C_1$–$C_6$ alkyl)OS(O)$_2$(tolyl) or ($C_1$–$C_6$ alkyl)OS(O)$_2$(phenyl)]. A base can be used in the reaction. Inorganic bases such as potassium carbonate and sodium hydride are preferred. The reaction is run in an inert solvent at about −10 to 60° C. Suitable solvents include ethers such as diethyl ether, tetrahydrofuran and dioxane, ketones such as acetone and ethyl methylketone, and esters such as ethyl and propyl acetate, aromatic hydrocarbons such as xylene, aliphatic hydrocarbons such as cyclohexane and hexane, and amides such as dimethylacetamide and dimethylformamide. After the reaction is complete, the product can be isolated by washing with water and evaporation of the organic solvent. The product is usually of sufficient purity to be used directly in the next step. In some instances, isolation of the product is not necessary and the reaction mixture containing the 2-alkylthio-4(3H)-quinazolinone can be used directly in the next step.

The 2-alkylthio-4(3H)-quinazolinone of Formula IId is converted to the 4(3H)-quinazolinone of Formula I by treatment with a metal alkoxide of Formula $M^+(^-OR^2)$ wherein M is lithium, sodium or potassium in an inert solvent (Scheme 12).

Scheme 12

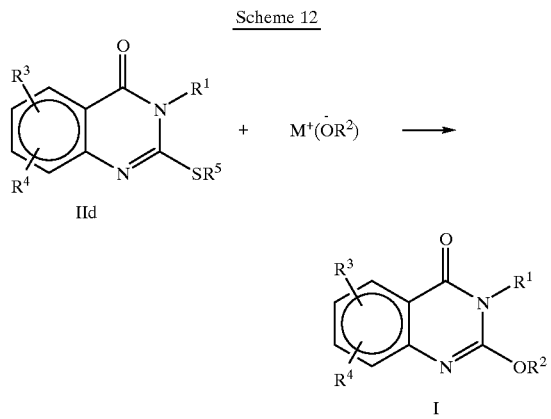

The metal alkoxide is generated as described above in Process A by treatment of the corresponding alcohol with a base such as sodium or potassium metal, sodium or potassium hydride, or sodium or potassium hydroxide. Only one equivalent of the metal alkoxide is required for the reaction; however, excess reagent can be used. Preferably, M is sodium or potassium and $R^2$ is propyl (i.e., sodium or potassium propoxide is employed).

Various solvents can be used including methanol, ethanol, n-propanol, i-propanol, methylene chloride, 1,2-dichloroethane, N,N-dimethylformamide, ethyl acetate, n-propyl acetate, i-propyl acetate, diethoxymethane, dimethoxyethane, tetrahydrofuran, dioxane, toluene, or xylene. If an ester or alcohol solvent is used, it is desirable to match the alkoxide with the ester group or alcohol to avoid the formation of a mixture of products. Ester solvents such as n-propyl acetate and aromatic solvents such as xylene are preferred.

The reaction is performed by adding the metal alkoxide to the 2-alkylthio-4(31H)-quinazolinone in a solvent at a temperature at about −30 to 50° C. Alternatively, the 2-alkylthio-4(3H)-quinazolinone can be added to a solution of the metal alkoxide. The preferred reaction temperature is from about −10 to 25° C. The reaction mixture is agitated until the 2-alkylthio-4(3H)-quinazolinone is consumed. If desired, the reaction can be run under I to 5 atmospheres ($1.013 \times 10^5$ to $5.065 \times 10^5$ Pa) of pressure. After the reaction is complete, the metal alkylthiolate is removed by washing with water, and the solvent is evaporated to afford the compound of Formula I.

Process D—beginning with Compounds of Formula 1b

Compounds of Formula I may be prepared by the sequence beginning with the reaction of the isothiocyanates of Formula 5 with alcohols of Formula 9 to produce intermediates of Formula 10.

Scheme 13

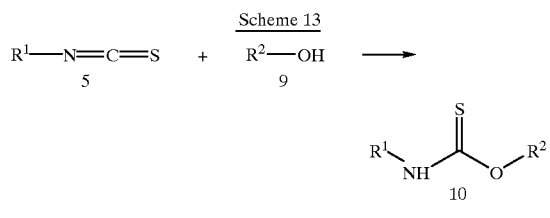

Isothiocyanates of Formula 5 are well-known in the art and can be prepared from the corresponding amines by treatment with thiophosgene (see e.g., *J. Heterocycl. Chem.*, (1990) 27, 407). The conversion of isothiocyanates of Formula 5 to products of Formula 10 has been cited in the art as well (*J. Econ. Entomol.*, (1985)78, 599). The reaction requires prolonged heating of equimolar amounts of an isothiocyanate and alcohol in an inert solvent at elevated temperatures in a pressure bomb apparatus. A preferable alternative for preparing compounds of Formula 10 from isothiocyanates 5 involves reacting the isothiocyanates in neat alcohols of Formula 9 at temperatures ranging from about 50 to 200° C. for about 0.5 to 24 h. Following concentration under reduced pressure, the crude material 10 may be purified by distillation at reduced pressure and/or silica gel chromatography; however, crude material of Formula 10 may be carried on without further purification. Materials of Formula 10 are well-known in the art and the skilled practitioner realizes that these compounds can also be prepared by other established means (see JP 5,139,901= CA, 119:154014v; Yakhak Hoe Chi, (1982),26, 91=CA, 97:162320; DE 2353976=CA, 83:78658; Chem. Zvesti, (1969) 23, 736=CA, 73:98568).

Conversion of the compounds of Formula 10 to intermediates of Formula 11 can be accomplished by reacting the compounds of Formula 10 (or anions thereof) with various alkylating agents in suitable solvents at ambient temperatures (Scheme 14). For example, the alkylating agents $(R^5)_3O^+BF_4^-$ are generally used in halocarbon or hydrocarbon solvents, $(R^5)_2SO_4$ in halocarbon, ether, or hydrocarbon solvents, and $R^5$—Y (where Y is I, Br, Cl) in alcohol, ether, halocarbon, hydrocarbon, amide, or sulfoxide solvents. Examples of bases which may be employed to optionally generate the anion of compounds of Formula 10 include NaH, NaOR², and $K_2CO_3$.

Scheme 14

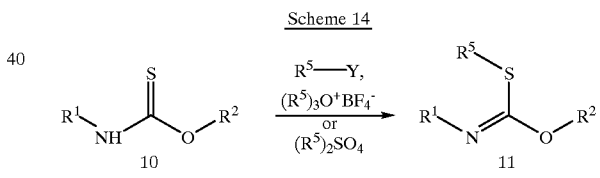

The reaction may be conducted for about 0.5 to 24 h at temperatures ranging from about ambient to 100° C. The mixture may then be subjected to aqueous extraction and concentration under reduced pressure to deliver the crude product of Formula 11 which may be suitable for further transformations. Additional purification, however, may be achieved by distillation at reduced pressure and/or silica gel chromatography.

Reaction of the intermediates of Formula 11 with compounds of Formula 1b yields the targeted compounds of Formula I (Scheme 15).

Scheme 15

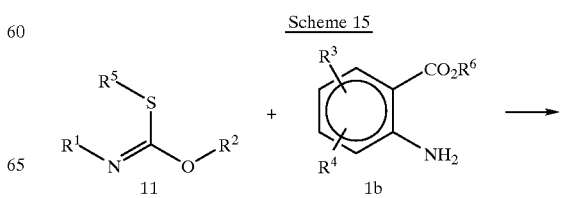

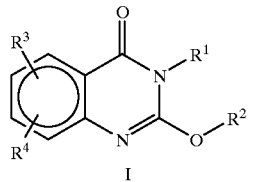

The reaction is conducted in the optional presence of a base (e.g.—Et₃N) in an alcohol, ether, or hydrocarbon solvent at temperatures ranging from about 25 to 200° C. for about 0.5 to 48 h. Purification of the final products of Formula I can be accomplished by silica-gel chromatography and/or recrystallization.

A preferable alternative for preparing compounds of Formula I from the isothiocyanates of Formula 5 involves the single-vessel preparation and utilization of compounds of Formula 11. The single-vessel preparation of materials similar to compounds of Formula 11 from isothiocyanates such as 5 and alkylating agents R⁵—Y has been documented in the art (*J. Am. Chem. Soc.*, (1983) 105, 6985 and *Ann. Chem.*, (1980)11, 1751). Thus, reaction of isothiocyanates 5 in neat alcohols of Formula 9 generates the intermediates of Formula 10 after heating at temperatures between about 50 to 200° C. for about 0.5 to 24 h. The resulting mixture is directly treated with base (e.g.—M⁺⁻OR², K₂CO₃, NaH) followed by an alkylating agent R⁵—Y at ambient temperature to afford the compounds of Formula 11 after reaction for about 0.5 to 24 h at 23 to 100IC. Finally, addition of the acid or ester species Ib in the optional presence of the aforementioned catalyst ultimately provides the targeted species of Formula I after further reaction, workup, and purification.

An alternative method for preparing a compound of Formula I is described by Schemes 16, and 17. A specifically preferred compound of Formula I, 6-iodo-3-n-propyl-2-n-propyloxy-4(3H)-quinazolinone is illustrated.

Contacting propylcarbonimidoyl dichloride, (H. Ulrich, *The Chemistry of Imidoyl Halides*, Chapter 2, Plenum Press, New York, 1968) in a suitable solvent such as methylene chloride with a base such as potassium hydroxide and propanol gives the propyl propylchloroformimidate IIIb, which is then contacted with 5-iodoanthranilic acid, a base such as potassium hydroxide and a catalytic amount of tetra-n-butylammonium iodide to give a 6-iodo-3-n-propyl-2-n-propyloxy-4(3H)-quinazolinone.

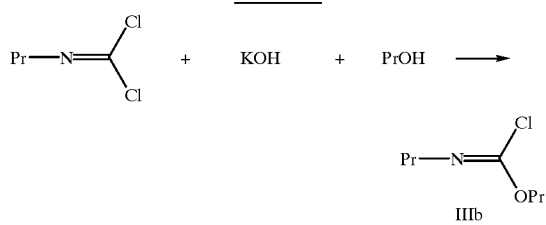

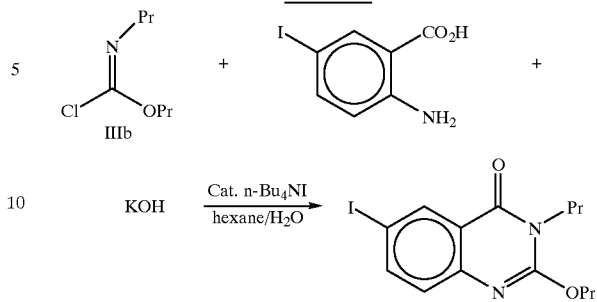

The isopropyl analog of the compound IIIb can be prepared by using the analogous starting materials isopropylcarbonimidoyl dichloride and isopropyl alcohol.

Process E—beginning with Compounds of Formula 1c

Compounds of Formula I may be prepared by a multi-step sequence beginning with the conversion of compounds of Formula 1c to isothiocyanates of Formula IV (Scheme 18).

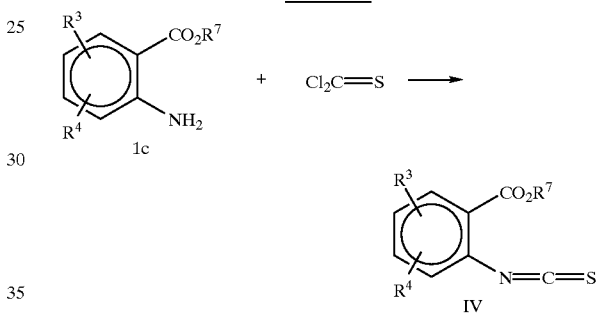

Examples of the esters 1c are cited in the literature (*J. Med. Chem.*, (1988) 31, 2136; *Acta. Chem. Scand.*, B42, (1988) 448; CA, 51:15522i), and the subsequent thiophosgene-mediated conversion of these types of esters to the corresponding isothiocyanates is documented as well (*J. Org. Chem.*, (1962) 27, 3701; *J. Med. Chem.*, (1991)34, 1531; *Pharmazie*, (1990) 45, 530).

Alternatively, isothiocyanates of Formula IV can be prepared by treating compounds of Formula 1c with carbon disulfide in the presence of base.

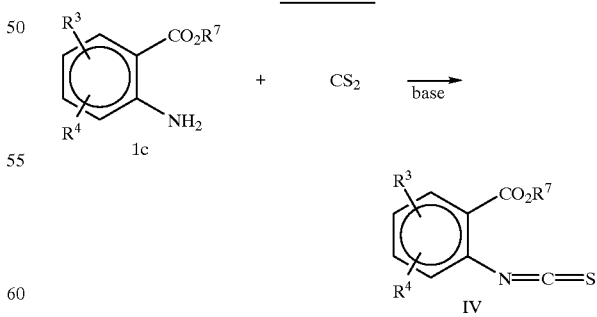

Either reaction may be conducted at temperatures ranging from about 25 to 150° C. for about 0.5 to 48 h in an inert solvent optionally in the presence of base (e.g.—Et₃N, solid or aqueous NaHCO₃). A preferable method employs a heterogeneous system comprised of a hydrocarbon solvent (e.g.—toluene, xylenes) and aqueous base [e.g.—NaHCO$_3$ (aq)] at ambient temperature for about 18 h. The skilled practitioner realizes that acid addition salts of compounds 1c, as well as the neutral species, may be utilized in this transformation. Upon completion of the reaction, the crude isothiocyanate IV may be used in subsequent reactions without further purification following phase separation, drying (Na$_2$SO$_4$), and concentration. However, isothiocyanates of Formula IV can be purified by additional aqueous washings, silica gel chromatography, and/or recrystallization from an appropriate solvent.

The subsequent conversion of isothiocyanates of Formula IV to compounds of Formula 4 can be achieved by treatment of compounds of Formula IV with alcohols of Formula 9 either neat or in an inert solvent at temperatures ranging from about 25 to 150° C. for about 0.5 to 48 h (Scheme 19). Similar transformations are known in the art (*J. Med. Chem.,* (1995) 38, (1922); *J. Het. Chem.,* (1982) 19, 1117). Purification of the compounds 4 can be achieved by precipitation and filtration from the reaction mixture, or by concentrating under reduced pressure followed by silica gel chromatography.

Scheme 19

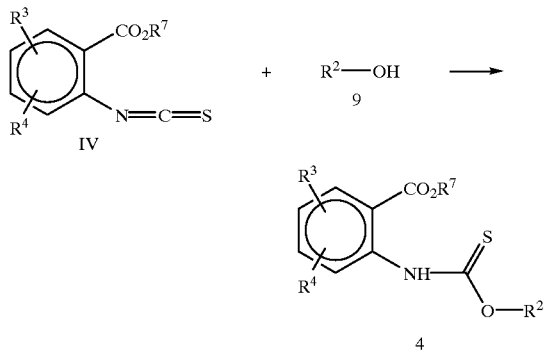

A preferable alternative for generating and utilizing the compounds of Formula 4 involves the neat reaction of the isothiocyanates IV with neat alcohols of Formula 9 at a reaction temperature from about 25 to 150° C. for about 18 h and treatment of the resulting reaction mixture with amines of Formula 6 to afford the compounds of Formula I which may subsequently be isolated directly from the reaction mixture via crystallization and filtration.

Scheme 20

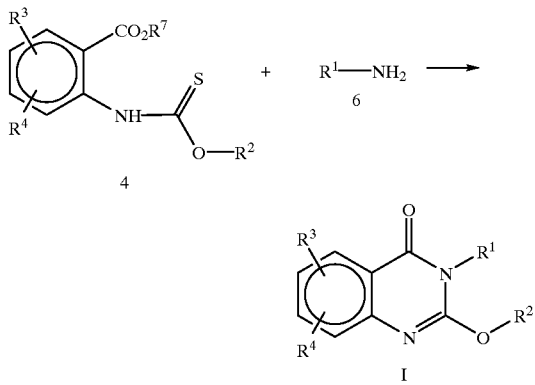

Alternatively, compounds of Formula 4 can be isolated and reacted with amines 6 in solvents other than the alcohols 9 to deliver the desired compounds I. Examples of such solvents include toluene, di-n-propyl ether, tetrahydrofuran, dimethylformamide, dimethylsulfoxide, and pyridine. The reaction may be conducted at temperatures ranging from about 25 to 200° C. for about 0.5 to 48 h. Purification of the crude product I so obtained may be accomplished by concentration under reduced pressure and silica gel chromatography.

EXAMPLE 1

Process A: Synthesis of 6-Iodo-2-propoxy-3-propyl-4 (3H)-quinazolinone

Step 1A: Synthesis of 2,3-Dihydro-6-iodo-3-propyl-2-thioxo-4(1H)-quinazolinone

To a slurry of 2-amino-5-iodobenzoic acid (100 g, 0.38 mol) in n-propyl acetate (315 mL) was added triethylamine (58 mL, 0.42 mol) at room temperature. The resulting solution was heated to reflux and n-propyl isothiocyanate (43 mL, 0.42 mol) was added over a one hour period. The reaction mixture was maintained at reflux for 18 h, then cooled to room temperature and filtered. The wetcake was washed with fresh propyl acetate and dried at 60° C. under vacuum. In this manner, 113 g of the title compound was obtained as a tan solid. m.p.>200° C.; $^1$H NMR (Me$_2$SO—d$_6$): δ13.02 (bs,1H), 8.22 (d,1H), 8.06 (dd,1H), 7.21 (d,1H), 4.34 (m,2H), 1.69 (m,2H), 0.93 (t,3H).

Step 1B: Synthesis of 2,3-Dihydro-6-iodo-3-propyl-2-thioxo-4(1H)-quinazolinone

To a slurry of 2-amino-5-iodobenzoic acid (20 g, 0.076 mol) in n-propyl acetate (63 mL) was added triethylamine (11.6 mL, 0.0.84 mol) followed by n-propyl isothiocyanate (8.7 mL, 0.084 mol) at room temperature. The resulting solution was heated to reflux and the water generated was removed in a Dean Stark trap. After 4 h, the reaction mixture was cooled to room temperature and filtered. The wetcake was washed with fresh n-propyl acetate and dried at 60° C. under vacuum. In this manner, 21.4 g of the title compound was obtained as a light tan solid. See Step 1A for $^1$H NMR data, the UV spectrum matched that of the material made previously.

Step 2A: Synthesis of 2-Chloro-6-iodo-3-propyl-4(3H)-quinazolinone 2,3-Dihydro-6-iodo-3-propyl-2-thioxo-4(1H)-quinazolinone (5 g, 0.014 mol) was slurried in n-propyl acetate and treated with phosgene (2.1 mL, 0.029 mol). The slurry was heated at reflux for 1 h. The excess phosgene was removed by co-distillation with n-propyl acetate at atmospheric pressure. The pot residue was then evaporated to dryness under vacuum. In this manner, 4.95 g of the title compound was obtained as a light pink solid. m.p. 98–100° C.; $^1$H NMR (Me$_2$SO-d$_6$): δ8.04 (d,1H), 8.16 (dd,1H), 7.31 (d,1H), 4.20 (m,2H), 1.78 (m,2H), 0.97 (t,3H).

Step 2B: Synthesis of 2-Chloro-6-iodo-3-propyl-4(3H)-quinazolinone 2,3-Dihydro-6-iodo-3-propyl-2-thioxo4(1H)-quinazolinone (50 g, 0.144 mol) was slurried in xylene (283 g) and heated to 85–90° C. Phosgene (12.0 mL, 0.159 mol) was added. Heating was continued until the thioquinazolinedione was consumed by thin layer chromatography analysis (340 minutes). The excess phosgene was removed by codistillation with xylene at atmospheric pressure. The distillation was ceased when the distillate weight reached 37.9 g. The solution was cooled to room temperature and used directly in Step 3.

Step 3: Synthesis of 6-Iodo-2-propoxy-3-propyl-4(3H)-quinazolinone

Sodium propoxide solution was prepared by combining sodium hydroxide (10 g, 0.25 mol) and n-propanol (90 g, 1.5 mol) and heating the slurry at reflux for 2 h. The resulting solution was cooled to room temperature and stored under $N_2$.

A portion of the sodium propoxide solution prepared above (87 g) was cooled to 1° C. and treated dropwise with the solution of 2-chloro-6-iodo-3-n-propyl-4(3H)-quinazolinone prepared in Step 2B above. The temperature was maintained at or below 0° C. and the addition took 2.5 h. After stirring at 0° C. for an additional 1.5 h, the reaction mixture was poured into 250 mL water. The phases were separated and the organic phase was washed two times each with 250 mL water. The organic phase was then evaporated under reduced pressure to give 53.4 g of a light yellow oil which solidified upon standing to a white solid. mp 60–62° C.; $^1$H NMR (CDCl$_3$): δ8.49 (d,1H), 7.87 (dd,1H), 7.19 (d,1H), 4.43 (t,2H), 4.05 (m,2H), 1.85 (m,2H), 1.70 (m,2H), 1.05 (t,3H), 0.96 (t,3H).

EXAMPLE 2

Process A: Synthesis of 6-Iodo-2-methoxy-3-propyl-4 (3H)-quinazolinone

2-Chloro-6-iodo-3-propyl-4(3H)-quinazolinone (about 1 g, 0.0029 moles) in n-propyl acetate (about 10 mL) was diluted with methyl acetate and cooled to 0° C. Sodium methoxide in methanol (25% by weight, 1.25 g, 0.0058 mol) was added. The slurry was stirred for 5 minutes, then diluted with methyl acetate and washed two-times with water. The organic phase was evaporated under reduced pressure, and the residue was recrystallized from hexanes. In this manner, 0.48 g of the title compound was obtained as a pink solid. m.p. 88–90° C.; $^1$H NMR (CDCl$_3$): δ8.50 (s,1H), 7.85 (dd,1H), 7.22 (d,1H), 4.06 (s,3H), 4.02 (m,2H), 1.55 (m,2H), 0.94 (t,3H); MS: 344 (M+), 302,272.

EXAMPLE 3

Process B: Synthesis of 6-Iodo-2-propoxy-3-propyl-4 (3H)-quinazolinone

To a slurry of 6-iodo-3-propyl-2,4(1H,3H)-quinazolinedione (1 g, 0.003 mol) in n-propanol (50 mL) was added potassium carbonate (3.03 g, 0.030 moles) and di-n-propyl sulfate (0.55 mL, 0.003 moles, TCI America). The reaction mixture was heated at reflux for 6 h, then cooled to room temperature and diluted with water (100 mL). The mixture was extracted two times with methylene chloride, and the organic phases were washed one time with brine. The organic phases were combined, dried (MgSO$_4$) and evaporated to a white solid (1 g). $^1$H NMR indicated a mixture of unreacted quinazoline-2,4-dione, the title compound, and the N-propyl isomer of the title compound.

EXAMPLE 4

Process D: Synthesis of 6-Iodo-2-propoxy-3-propyl-4 (3H)-quinazolinone

Step A: Preparation of O-Propyl propylcarbamothioate

To 10 g (0.099 g) of propyl isothiocyanate was added 50 mL of n-propanol. The reaction mixture was heated to reflux for 3 h and cooled to room temperature. An aliquot was removed and concentrated under reduced pressure to give the title compound, $^1$H NMR (300 MHz, CDCl$_3$): δ0.94–1.02 (m,6H); 1.49–1.83 (m,4H); 3.22 (q), 3.51 (q,2H total); 4.37 (t), 4.45 (t,2H total), 6.25 (br s), 6.78 (br s,1H total). The remaining reaction mixture was concentrated under reduced pressure as above to provide 13.5 g of oil which was used without further purification.

Step B: Preparation of S-Methyl O-propyl propylcarbonimidothioate

To a solution of 5 g (0.031 moles) of 0-propyl propylcarbamothioate in 155 mL of tetrahydrofuran was added 1.37 g (0.034 moles) of 60% NaH at 0–5° C. After allowing the mixture to warm to room temperature, 2.49 mL (0.040 moles) of iodomethane was added and the reaction was stirred for 2 h. The reaction was partitioned between 200 mL each of diethyl ether and saturated aqueous sodium bicarbonate. The organic phase was separated, washed with water and brine, dried over anhydrous sodium sulfate, and concentrated under reduced pressure to deliver 5.9 g of the title compound, which was carried on without further purification, $^1$H NMR (400 MHz, CDCl$_3$): δ0.91–0.99 (m,6H); 1.56–1.62 (m,2H); 1.68–1.75 (m,2H); 2.38 (s,3H); 3.14 (t,2H); 4.09 (t,2H).

Step C: Preparation of $^6$-Iodo-$^2$-propoxy-3-propyl-4(3H)-quinazolinone

To a solution of 0.38 g (1.44 mmoles) of 2-amino-5-iodobenzoic acid and 0.14 g (1.38 mmol) of triethylamine in 7.15 mL of n-propanol was added 0.25 g (1.143 mmol) of S-methyl O-propyl propylcarbonimidothioate. The reaction mixture was stirred at room temperature for 18 h, heated to 60° C. for 24 h, and then heated to reflux for 6 h. The reaction was then concentrated under reduced pressure to give about 0.6 g of crude material, which was purified by flash chromatography on silica (93:7 hexanes:ethyl acetate) to give 0.21 g of the title compound, $^1$H NMR (400 MHz, CDCl$_3$): δ0.96 (t,3H); 1.06 (t,3H); 1.64–1.79 (m,2H); 1.81–1.92 (m,2H); 4.05 (t,2H); 4.43 (t,2H), 7.19 (d,1H); 7.85 (dd,1H); 8.49 (d,1H). In addition, 0.11 g of propyl-5-iodoanthranilate was obtained from the flash chromatography, $^1$H NMR (400 MHz, CDCl$_3$): δ1.02 (t,3H); 1.76–1.86 (m,2H); 4.23 (t,2H); 5.8 (br s,2H); 6.45 (d,1H); 7.45 (dd, 1H); 8.13 (d,1H).

EXAMPLE 5

Process D: Synthesis of $^6$-Iodo-$^2$-propoxy-3-propyl-4 (3H)-quinazolinone

Step A: Preparation of Propyl propylchloroformimidate

To a stirred solution of propylcarbonimidoyl dichloride (1.2 g, 8.57 mmol) in dichloromethane (3 mL) cooled to -5–0° C., potassium propoxide (prepared from potassium hydroxide and propanol and removing water by azeotrope) in propanol was added dropwise, keeping the reaction temperature at about 0° C. The transformation of the C=N absorption at 1650 cm$^{-1}$ for propylcarbonimidoyl dichloride to 1697 cm$^{-1}$ for propyl propylchloroformimidate was monitored by IR. When the reaction was complete, the reaction mixture was poured into water (10 mL) and extracted with diethyl ether (3 times with 10 mL). The diethyl ether extracts were combined, dried (MgSO$_4$), and concentrated under reduced pressure to give propyl propylchloroformimidate (1.35 g, 96%, oil; b.p. 61–62° C. (1.3× 10$^3$ Pa). IR (CCl$_4$): 2966.8, 1697.4, 1186.4 cm$^{-1}$.

Step B: Preparation of 6-Iodo-2-propoxy-3-propyl-4(3H)-quinazolinone from 5Iodoanthranilic acid and Propyl propylchloroformimidate To a vigorously stirred mixture of 5-iodoanthranilic acid (1 g, 3.8 mmol), potassium hydroxide (0.8 g, 14.3 mmol) and a catalytic amount of tetra-n-butylammonium iodide in water (8 mL) at 20° C., propyl propylchloroformimidate (1.37 g, 8.38 mmole) in hexane (4 mL) was added. The reaction was stirred vigorously and the reaction temperature was maintained between 20–25° C. with the use of an external water bath. The reaction was monitored by TLC. After 15 min of stirring, hexane (10 mL) was added. The aqueous layer was separated and extracted with hexane (10 mL). The combined hexane layers were washed with HCl (5 mL), saturated aqueous $NaHCO_3$ (5 mL), and water (5 mL); dried over magnesium sulfate; suction filtered; and concentrated under reduced pressure to an oil which was purified by silica gel column (eluted with ethyl acetate/hexane=⅛) to provide the product (1.2 g, 85%). Recrystallization from 1-propanol/water gave a crystalline white solid (m.p. 51.5° C.). $^1H$ NMR (in $CDCl_3$)δ: 0.97 (t,3H), 1.06 (t,3H), 1.66 (m,2H), 1.85 (m,2H), 4.06 (t,2H), 4.43 (t,2H), 7.18 (d,1H), 7.84 (dd,1H), 8.48 (d,1H).

EXAMPLE 6

Process E: Synthesis of 6-Iodo-3-propyl-2-propyloxy-4 (3H)-quinazolinone

Step A: Preparation of Methyl 2-amino-5-iodobenzoate hydrochloride

To a solution of 25 g (0.165 mol) of methyl 2-aminobenzoate in 3 L of glacial acetic acid was added a second solution of 26.82 g (0.165 mol) iodine monochloride in 250 mL of glacial acetic acid over 20–30 min. The resulting mixture was stirred at room temperature for 24 h. The ensuing precipitate was filtered, washed with glacial acetic acid followed by diethyl ether, and dried to provide 43.2 g of the title compound, which was generally used without further purification in subsequent steps, m.p. 188–192° C.; $^1H$ NMR (300 MHz, $Me_2SO$—$d_6$): δ3.79 (s,3H); 6.67 (d,1H); 7.50 (dd,1H); 7.93 (d,1H). Anal. Calcd. for $C_8H_9NO_2ICl$: C, 30.65; H, 2.89; N, 4.47; O, 10.21; Cl, 11.31; I, 40.48. Found: C, 31.19; H, 2.85; N, 4.48; 0, 10.27; Cl, 11.72; I, 40.15.

A 0.5 g (1.60 mmoles) sample of the above hydrochloride salt in 50 mL of dichloromethane was extracted with 50 mL of 1M sodium hydroxide. The organic phase was separated, dried over anhydrous sodium sulfate, and concentrated under reduced pressure to deliver 0.4 g (1.44 mmol) of methyl 2-amino-5-iodobenzoate, m.p. 83–85° C. (lit[1]. m.p. 83–85° C.); $^1H$ NMR (300 MHz, $Me_2SO$-$d_6$): δ3.79(s,3H); 6.64 (d,1H); 6.79 (br s,2H); 7.49 (dd,1H); 7.93(d,1H). ([1]J. Med. Chem., '88,31, 2136 and refs. therein.)

Step B: Preparation of Methyl 5-iodo-2-isothiocyanatobenzoate

To 20 g (0.064 mol) of methyl 2-amino-5-iodobenzoate hydrochloride was added 720 mL of toluene, 180 mL of water, 49 g (0.593 mol) of sodium bicarbonate, and 13.2 mL (0.181 mol) of thiophosgene. The biphasic mixture was stirred at room temperature overnight, diluted with 400 mL of water, and the phases were separated. The organic phase was washed with brine, dried over anhydrous sodium sulfate, and concentrated under reduced pressure to deliver 21.43 g of the title compound, which was used without further purification, $^1H$ NMR (300 MHz, $CDCl_3$): δ3.97 (s,3H); 7.02 (d,1H); 7.81 (dd,1H); 8.30 (d,1H). An analytical sample was prepared by treating 0.30 g of the crude material with 5 mL of n-propanol, followed by the dropwise addition of water. The ensuing precipitate was filtered to deliver 259 mgs of purified methyl 5-iodo-2-isothiocyanatobenzoate, m.p. 60–62° C.

Step C: Preparation of Methyl 5-iodo-2-[(nronoxythioxomethyl)-amino]benzoate

To 18.66 g (0.058 mol) of methyl 5-iodo-2-isothiocyanatobenzoate was added 330 mL of n-propanol. The reaction solution was heated at reflux overnight and cooled to room temperature. A 10 mL sample of the reaction mixture was removed and purified by flash chromatography on silica gel (95:5 hexanes:ethyl acetate) to give 0.48 g of the title compound, m.p. 45–47° C.; $^1H$ NMR (300 MHz, $CDCl_3$): δ1.02 (t,3H); 1.80–1.91 (m,2H); 3.95 (s,3H); 4.51 (t,2H); 7.81 (dd,1H); 8.15–8.45 (m,2H); 11.62 (br s,1H).

The remaining reaction mixture (320 mL) was taken directly on as described in Step D.

Step D: Preparation of 6-Iodo-2-propoxy-3-propyl-4(3H)-quinazolinone

To the remaining 320 mL solution of methyl 5-iodo-2-[(propoxythioxomethyl)amino]benzoate from Step C above was added 10.86 mL (0.132 mol) of propylamine. The reaction solution was heated at reflux overnight, concentrated to ⅓ volume under reduced pressure, and treated with 75 mL water added dropwise at room temperature. Following refrigeration at 0–5° C. overnight, an additional 25 mL $H_2O$ was added and cooling was continued for an additional 48 h. Filtration of the ensuing mixture provided 15.68 g of the title compound, $^1H$ NMR (300 MHz, $CDCl_3$): δ0.96 (t,3H); 1.06 (t,3H); 1.64–1.79 (m,2H); 1.81–1.92 (m,2H); 4.05 (t,2H); 4.43 (t,2H); 7.19 (d,1H); 7.85 (dd,1H); 8.49 (d,1H), m.p. 49–53° C.

EXAMPLE 7

Process A Intermediate: Synthesis of 2,3-Dihydro-6-iodo-3-propyl-2-thioxo-4(1H)-quinazolinone Carbon disulfide (16.4 mL, 0.28 mole) was added to a solution of potassium hydroxide (18.4 g, 0.28 mol) in water (100 mL). The reaction mixture was then cooled to 1 1° C. and n-propylamine (16.6 g, 0.28 mol) was added. An exotherm to 14° C. was observed and the reaction mixture became an orange slurry. The mixture was heated at 60° C. for 1 h and then cooled to 17° C. Ethyl chloroformate (32 g, 0.30 mole) was then added over a 30 min period allowing the temperature to rise to 25° C. Additional potassium hydroxide (9.2 g, 0.14 mol) was then added. After stirring for 20 min, 5-iodoanthranilic acid (26.4 g, 0.10 mol) was added and the resulting tan slurry was heated to 75° C. After 4.5 h, the reaction mixture was cooled to room temperature. Concentrated aqueous HCl was added to reduce the pH from 10 to 2. The aqueous phase was decanted from the oily solids, and the solids were washed two times with water (100 mL each). Methanol (100 mL) was added to crystallize the produce. The solids were recovered by filtration, washed with methanol (2 times with 15 mL), and dried. The 2,3-dihydro-6-iodo-3-propyl-2-thioxo-4(1H)-quinazolinone weighed 27.8 g and had a melting point of 267–269° C.

EXAMPLE 8

Process C: 6-Iodo-2-(methylthio)-3-propyl-4(3H)-quinazolinone

Sodium hydride (60% dispersion in oil, 34.8 g, 0.87 mol) was washed two-times with hexanes. The washed sodium hydride was then slurried in tetrahydrofuran (1.3 L) and stirred 5 min. 6-Iodo-3-n-propyl-2-thio-4(3H)-quinazolinedione (300 g, 0.87 mol) was added portionwise as a solid and stirred for 15 min. Iodomethane (129 g, 0.91 mol) dissolved in tetrahydrofuran (100 mL) was then added dropwise. The reaction mixture was stirred at room temperature overnight. Approximately one half of the solvent was removed under reduced pressure, and the resulting slurry was diluted with water (3L). After stirring for 20 min, the solids were removed by filtration and washed twice with water and once with hexanes. The solids were dried under vacuum at 50° C. to afford 281.3 g of the title compound as an off-white solid. $^1H$ NMR ($CDCl_3$): δ8.5 (d,1H), 7.9 (dd,1H), 7.25 (d,1H), 4.05 (t,2H), 2.63 (s,3H), 1.8 (m,2H), 1.0 (t,3H).

EXAMPLE 9

Process C: Synthesis of 6-Iodo-2-propoxy-3-propyl-4(3H)-quinazolinone

Sodium hydride (60% dispersion in oil, 164.0 g, 4.10 mol) was washed two times with hexanes. The washed sodium hydride was slurried in tetrahydrofuran (4.5 L) under nitrogen. To this suspension was added dropwise 1-propanol (246.0 g, 4.10 mol) dissolved in tetrahydrofuran (0.5 L). The mixture was stirred at room temperature until gas evolution and foaming ceased. 6-Iodo-2-(methylthio)-3-propyl-4(3H)-quinazolinone (295.2 g, 0.82 mol) was then added portionwise as a solid and the mixture was stirred overnight. The following day, water (approximately 0.5 L) was added dropwise, cautiously. Most of the tetrahydrofuran was evaporated under reduced pressure and then water (4 L) was added. The mixture was extracted two-times with diethyl ether (4 L and 2 L), and the combined ether extracts were washed two times with water (2 L). The organic layer was dried over MgSO4 with charcoal, filtered through CELITE, and evaporated under reduced pressure. The residue crystallized and was triturated with hexane. The solid was dissolved in additional hexane with light heating, and a small amount of undissolved solids were removed by filtration. The solids which formed in the filtrate upon cooling were filtered, washed with cold hexanes, and dried on the filter with a heavy nitrogen stream.

A second batch was run in the same manner using 857.0 g (2.38 mol) of 6-iodo-2-(methylthio)-3-propyl-4(3H)-quinazolinone and 2 L of water for the quench. A second crop of crystals were isolated from the final hexane filtration. The products were combined to give 973.1 g of the title compound added portionwise as a solid and the mixture was stirred overnight. The following day, water (approximately 0.5 L) was added dropwise, cautiously. Most of the tetrahydrofuran was evaporated under reduced pressure and then water (4 L) was added. The mixture was extracted two-times with diethyl ether (4 L and 2 L), and the combined ether extracts were washed two times with water (2 L). The organic layer was dried over MgSO4 with charcoal, filtered through CELITE, and evaporated under reduced pressure. The residue crystallized and was triturated with hexane. The solid was dissolved in additional hexane with light heating, and a small amount of undissolved solids were removed by filtration. The solids which formed in the filtrate upon cooling were filtered, washed with cold hexanes, and dried on the filter with a heavy nitrogen stream. A second crop of crystals were isolated from the final hexane filtration. The products were combined to give 973.1 g of the title compound which was 99.95% pure by LC area percent. $^1$H NMR (CDCl3): 8.5 (d,1H), 7.85 (dd,1H), 7.2 (d,1H), 4.45 (t,2H), 4.05 (t,2H), 1.85 (m,2H), 1.7 (m,2H), 1.05 (t,3H), 0.95 (t,3H).

EXAMPLE 10

Process B Intermediate: 6-Iodo-3-propyl-2,4(1H,3H)-quinazolinedione

A mixture of 5.0 g (0.019 mol) 2-amino-5-iodobenzoic acid, 1.9 g (0.012 mol) n-propyl isocyanate, and 1.9 g (0.019 mol) triethylamine in 190 mL of acetonitrile was stirred at ambient temperature overnight. An additional 1.9 g (0.012 mol) of n-propyl isocyanate was added and stirring continued at ambient temperature for an additional 72 h. The reaction was then concentrated by atmospheric pressure distillation to deliver 7.8 g of an oil which solidified upon standing under reduced pressure. A 3.6 g portion of this crude material was subjected to heating neat at 190° C. for 0.75 h. The resulting reaction mass was cooled, treated with approximately 20 mL ethanol, agitated, and filtered. The filter cake was subsequently washed with ether and dried to deliver 1.8 g of the title compound, $^1$H NMR (300 MHz, Me$_2$SO—d$_6$): δ0.87 (s,3H); 1.50–1.69 (m,2H); 3.83 (t,2H); 6.99 (d,1H); 7.94 (dd,1H); 8.16 (d,1H); 11.50 (bs,1H).

EXAMPLE 11

Process A Intermediate: Synthesis of $^6$-Iodo-$^2$-propoxy-3-propyl-4(3H)-quinazolinone Step A: Preparation of 6-Iodo-2H-3,1-benzoxazine-2,4(1H)-dione A mixture of 2-amino-5-iodobenzoic acid (25 g, 95.05 mmol) and triphosgene (77.1 g, 260.4 mmol) in dioxane (316 mL) was heated to reflux for 8 h. The resulting solid was filtered and washed with diethyl ether to give 28.1 g of the title compound, $^1$H NMR (300 MHz, Me$_2$SO-d$_6$): δ6.96 (d,1H); 8.02 (dd,1H); 8.13 (d,1H); 11.82 (br s,1H); m/e 288 deprotonated parent molecular ion (m/e) measured by mass spectrometry using atmospheric pressure chemical ionization in the negative ion mode (APCI$^-$).

Step B: Preparation of 2-Amino-5-iodo-N-propylbenzamide

Propylamine (1.2 g, 20.3 mmol) and 6-iodo-2H-3,1-benzoxazine-2,4(1H)-dione (5.0 g, 17.3 mmol) were combined in pyridine (85 mL) and stirred at room temperature for 24 h. The reaction was concentrated under reduced pressure and the resulting residue was partitioned between ethyl acetate (200 mL) and 5% hydrochloric acid (200 mL). The phases were separated and the organic phase was washed with 1N sodium hydroxide, water, and brine. Drying over anhydrous sodium sulfate and evaporation under reduced pressure afforded 3.9 g of the title compound, $^1$H NMR (300 MHz, CDCl$_3$): δ0.99 (t,3H1); 1.63 (m,2H); 3.35 (m,2H); 5.52 (br s,2H); 5.95 (br s,1H); 6.47 (d, 1H); 7.42 (dd,1H); 7.55(d,1H).

Step C: Preparation of 2,3-Dihydro-6-iodo-3-propyl-2-thioxo-4(1H)-quinazolinone

To a solution of 2-amino-5-iodo-N-propylbenzamide (1.0 g, 3.1 mmol) and carbon disulfide (0.59 g, 9.38 mmol) in dimethylformamide (3.1 mL) was added potassium carbonate (0.43g, 3.1 mmol). The reaction mixture was heated to reflux for 2 h, cooled to room temperature, and added dropwise to 1N hydrochloric acid (25 mL). The resulting precipitate was filtered, washed with water (2×10 mL), methanol (2×10 mL) and diethyl ether (10 mL), and dried to deliver 1.04 g of the title compound, m.p. 267–269° C.; $^1$H NMR (300 MHz, Me$_2$SO-d$_6$): δ0.90 (t,3H); 1.68 (m,2H); 4.33 (t,2H); 7.18 (d,1H); 8.04 (dd,1H); 8.19 (d, 1H); 12.98 (s, 1H).

Using the procedures outlined in Schemes 1–20 and Examples 1–11, the compounds of Tables I, Ia, Ib, Ic, Id, II, III, IV and V can be prepared.

TABLE I 3-propyl-2-(propyloxy)-4(3H)-quinazolinone
2-ethoxy-6-iodo-3-propyl-4(3H)-quinazolinone
6-iodo-2-methoxy-3-propyl-4(3H)-quinazolinone
3-ethyl-6-iodo-2-(propyloxy)-4(3H)-quinazolinone
6-iodo-3-methyl-2-(propyloxy)-4(3H)-quinazolinone
6-iodo-2-(2-propenyloxy)-3-(propyl)-4(3H)-quinazolinone
6-iodo-3-(2-propenyl)-2-(propyloxy)-4(3H)-quinazolinone
3-ethyl-1,2-dihydro-6-iodo-2-thioxo-4(3H)-quinazolinone
2-chloro-3-ethyl-6-iodo-4(3H)-quinazolinone
2-chloro-6-iodo-3-methyl-4(3H)-quinazolinone
3-ethyl-6-iodo-2,4-(1H,3H)-quinazolinedione

TABLE I-continued 6-iodo-3-methyl-2,4-(1H,3H)-quinazolinedione
2-(ethylthio)-6-iodo-3-propyl-4(3H)-quinazolinone
3-ethyl-6-iodo-2-(methylthio)-4(3H)-quinazolinone
6,8-diiodo-3-propyl-2-propyloxy-4(3H)-quinazolinone
3-(cyclopropylmethyl)-6-iodo-2-propyloxy-4(3H)-quinazolinone

TABLE IA

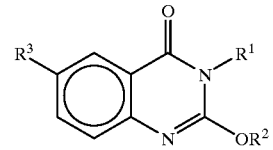

| Compound No. | R³ | R¹ | R² |
|---|---|---|---|
| 1 | I | CH₃ | CH₃ |
| 2 | I | CH₂CH₃ | CH₃ |
| 3 | I | CH₂CH₂CH₃ | CH₃ |
| 4 | I | CH₂(CH₂)₂CH₃ | CH₃ |
| 5 | I | CH₃ | CH₂CH₃ |
| 6 | I | CH₂CH₃ | CH₂CH₃ |
| 7 | I | CH₂CH₂CH₃ | CH₂CH₃ |
| 8 | I | CH₃ | CH₂CH₂CH₃ |
| 9 | I | CH₂CH₃ | CH₂CH₂CH₃ |
| 10 | I | CH₃ | CH₂(CH₂)₂CH₃ |
| 11 | Br | CH₃ | CH₃ |
| 12 | Br | CH₂CH₃ | CH₃ |
| 13 | Br | CH₂CH₂CH₃ | CH₃ |
| 14 | Br | CH₂(CH₂)₂CH₃ | CH₃ |
| 15 | Br | CH₃ | CH₂CH₃ |
| 16 | Br | CH₂CH₃ | CH₂CH₃ |
| 17 | Br | CH₂CH₂CH₃ | CH₂CH₃ |
| 18 | Br | CH₃ | CH₂CH₂CH₃ |
| 19 | Br | CH₂CH₃ | CH₂CH₂CH₃ |
| 20 | Br | CH₃ | CH₂(CH₂)₂CH₃ |
| 21 | I | CH(CH₃)₂ | CH₃ |
| 22 | I | CH(CH₃)₂ | CH₂CH₃ |
| 23 | I | CH(CH₃)₂ | CH(CH₃)₂ |
| 24 | I | CH₃ | CH(CH₃)₂ |
| 25 | I | CH₂CH₃ | CH(CH₃)₂ |
| 26 | I | CH(CH₃)₂ | CH(CH₃)₂ |
| 27 | I | C(CH₃)₃ | CH₃ |
| 28 | I | C(CH₃)₃ | CH₂CH₃ |
| 29 | I | C(CH₃)₃ | CH(CH₃)₂ |
| 30 | I | C(CH₃)₃ | C(CH₃)₃ |
| 31 | I | CH₃ | C(CH₃)₃ |
| 32 | I | CH₂CH₃ | C(CH₃)₃ |
| 33 | I | CH(CH₃)₂ | C(CH₃)₃ |
| 34 | I | C(CH₃)₃ | C(CH₃)₃ |
| 35 | Br | CH(CH₃)₂ | CH₃ |
| 36 | Br | CH(CH₃)₂ | CH₂CH₃ |
| 37 | Br | CH(CH₃)₂ | CH(CH₃)₂ |
| 38 | Br | CH₃ | CH(CH₃)₂ |
| 39 | Br | CH₂CH₃ | CH(CH₃)₂ |
| 40 | Br | CH(CH₃)₂ | CH(CH₃)₂ |
| 41 | Br | C(CH₃)₃ | CH₃ |
| 42 | Br | C(CH₃)₃ | CH₂CH₃ |
| 43 | Br | C(CH₃)₃ | CH(CH₃)₂ |
| 44 | Br | C(CH₃)₃ | C(CH₃)₃ |
| 45 | Br | CH₃ | C(CH₃)₃ |
| 46 | Br | CH₂CH₃ | C(CH₃)₃ |
| 47 | Br | CH(CH₃)₂ | C(CH₃)₃ |
| 48 | Br | C(CH₃)₃ | C(CH₃)₃ |
| 49 | I | CH₂CH(CH₃)₂ | CH₃ |
| 50 | I | CH₂CH(CH₃)₂ | CH₂CH₃ |
| 51 | I | CH₂CH(CH₃)₂ | CH(CH₃)₂ |
| 52 | I | CH₃ | CH₂CH(CH₃)₂ |
| 53 | I | CH₂CH₃ | CH₂CH(CH₃)₂ |
| 54 | I | CH(CH₃)₂ | CH₂CH(CH₃)₂ |
| 55 | 1 | CH₂CH(CH₃)₂ | CH₂CH(CH₃)₂ |
| 56 | I | CH₂C(CH₃)₃ | CH₃ |
| 57 | I | CH₂C(CH₃)₃ | CH₂CH₃ |

TABLE IA-continued

| Compound No. | R³ | R¹ | R² |
|---|---|---|---|
| 58 | I | CH₂C(CH₃)₃ | CH(CH₃)₂ |
| 59 | 1 | CH₂C(CH₃)₃ | C(CH₃)₃ |
| 60 | 1 | CH₃ | CH₂C(CH₃)₃ |
| 61 | I | CH₂CH₃ | CH₂C(CH₃)₃ |
| 62 | I | CH(CH₃)₂ | CH₂C(CH₃)₃ |
| 63 | I | C(CH₃)₃ | CH₂C(CH₃)₃ |
| 64 | Br | CH₂CH(CH₃)₂ | CH₃ |
| 65 | Br | CH₂CH(CH₃)₂ | CH₂CH₃ |
| 66 | Br | CH₂CH(CH₃)₂ | CH(CH₃)₂ |
| 67 | Br | CH₃ | CH₂CH(CH₃)₂ |
| 68 | Br | CH₂CH₃ | CH₂CH(CH₃)₂ |
| 69 | Br | CH(CH₃)₂ | CH₂CH(CH₃)₂ |
| 70 | Br | CH₂CH(CH₃)₂ | CH₂CH(CH₃)₂ |
| 71 | Br | CH₂C(CH₃)₃ | CH₃ |
| 72 | Br | CH₂C(CH₃)₃ | CH₂CH₃ |
| 73 | Br | CH₂C(CH₃)₃ | CH(CH₃)₂ |
| 74 | Br | CH₂C(CH₃)₃ | C(CH₃)₃ |
| 75 | Br | CH₃ | CH₂C(CH₃)₃ |
| 76 | Br | CH₂CH₃ | CH₂C(CH₃)₃ |
| 77 | Br | CH(CH₃)₂ | CH₂C(CH₃)₃ |
| 78 | Br | C(CH₃)₃ | CH₂C(CH₃)₃ |
| 79 | I | CH₂CH(cyclopropyl) | CH₃ |
| 80 | I | CH₂CH(cyclopropyl) | CH₂CH₃ |
| 81 | I | CH₂CH(cyclopropyl) | CH₂CH₂CH₃ |
| 82 | I | CH₃ | CH₂CH(cyclopropyl) |
| 83 | I | CH₂CH₃ | CH₂CH(cyclopropyl) |
| 84 | I | CH₂CH₂CH₃ | CH₂CH(cyclopropyl) |
| 85 | I | cyclobutyl | CH₃ |
| 86 | I | cyclobutyl | CH₂CH₃ |
| 87 | I | cyclobutyl | CH₂CH₂CH₃ |

TABLE IA-continued

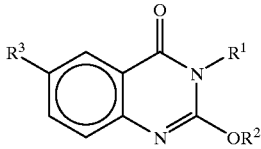

| Compound No. | R³ | R¹ | R² |
|---|---|---|---|
| 88 | I | CH₃ | CH₂—CH₂<br>\|    \|<br>CH—CH₂ |
| 89 | I | CH₂CH₃ | CH₂—CH₂<br>\|    \|<br>CH—CH₂ |
| 90 | I | CH₂CH₂CH₃ | CH₂—CH₂<br>\|    \|<br>CH—CH₂ |
| 91 | I | CH(cyclobutyl CH₂—CH₂/CH₂—CH₂) | CH₃ |
| 92 | I | CH(cyclobutyl) | CH₂CH₃ |
| 93 | I | CH(cyclobutyl) | CH₂CH₂CH₃ |
| 94 | I | CH₃ | CH(cyclobutyl) |
| 95 | I | CH₂CH₃ | CH(cyclobutyl) |
| 96 | I | CH₂CH₂CH₃ | CH(cyclobutyl) |

TABLE IB

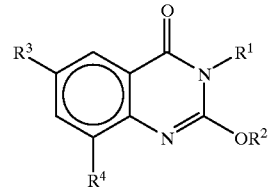

| Compound No. | R³ | R⁴ | R¹ | R² |
|---|---|---|---|---|
| 97 | I | I | CH₃ | CH₃ |
| 98 | I | I | CH₂CH₃ | CH₃ |
| 99 | I | I | CH₂CH₂CH₃ | CH₃ |
| 100 | I | I | CH₂(CH₂)₂CH₃ | CH₃ |
| 101 | I | I | CH₃ | CH₂CH₃ |
| 102 | I | I | CH₂CH₃ | CH₂CH₃ |
| 103 | I | I | CH₂CH₂CH₃ | CH₂CH₃ |
| 104 | I | I | CH₃ | CH₂CH₂CH₃ |
| 105 | I | I | CH₂CH₃ | CH₂CH₂CH₃ |
| 106 | I | I | CH₃ | CH₂(CH₂)₂CH₃ |
| 107 | Br | Br | CH₃ | CH₃ |
| 108 | Br | Br | CH₂CH₃ | CH₃ |
| 109 | Br | Br | CH₂CH₂CH₃ | CH₃ |
| 110 | Br | Br | CH₂(CH₂)₂CH₃ | CH₃ |
| 111 | Br | Br | CH₃ | CH₂CH₃ |
| 112 | Br | Br | CH₂CH₃ | CH₂CH₃ |
| 113 | Br | Br | CH₂CH₂CH₃ | CH₂CH₃ |
| 114 | Br | Br | CH₃ | CH₂CH₂CH₃ |
| 115 | Br | Br | CH₂CH₃ | CH₂CH₂CH₃ |
| 116 | Br | Br | CH₃ | CH₂(CH₂)₂CH₃ |
| 117 | I | Br | CH₃ | CH₃ |
| 118 | Br | I | CH₃ | CH₃ |
| 119 | I | Br | CH₃ | CH₂CH₂CH₃ |
| 120 | I | I | CH(CH₃)₂ | CH₃ |
| 121 | I | I | CH(CH₃)₂ | CH₂CH₃ |
| 122 | I | I | CH(CH₃)₂ | CH(CH₃)₂ |
| 123 | I | I | CH₃ | CH(CH₃)₂ |
| 124 | I | I | CH₂CH₃ | CH(CH₃)₂ |
| 125 | I | I | CH(CH₃)₂ | CH(CH₃)₂ |
| 126 | I | I | C(CH₃)₃ | CH₃ |
| 127 | I | I | C(CH₃)₃ | CH₂CH₃ |
| 128 | I | I | C(CH₃)₃ | CH(CH₃)₂ |
| 129 | I | I | C(CH₃)₃ | C(CH₃)₃ |
| 130 | I | I | CH₃ | C(CH₃)₃ |
| 131 | I | I | CH₂CH₃ | C(CH₃)₃ |
| 132 | I | I | CH(CH₃)₂ | C(CH₃)₃ |
| 133 | I | I | C(CH₃)₃ | C(CH₃)₃ |
| 134 | Br | Br | CH(CH₃)₂ | CH₃ |
| 135 | Br | Br | CH(CH₃)₂ | CH₂CH₃ |
| 136 | Br | Br | CH(CH₃)₂ | CH(CH₃)₂ |
| 137 | Br | Br | CH₃ | CH(CH₃)₂ |
| 138 | Br | Br | CH₂CH₃ | CH(CH₃)₂ |
| 139 | Br | Br | CH(CH₃)₂ | CH(CH₃)₂ |
| 140 | Br | Br | C(CH₃)₃ | CH₃ |
| 141 | Br | Br | C(CH₃)₃ | CH₂CH₃ |
| 142 | Br | Br | C(CH₃)₃ | CH(CH₃)₂ |
| 143 | Br | Br | C(CH₃)₃ | C(CH₃)₃ |
| 144 | Br | Br | CH₃ | C(CH₃)₃ |
| 145 | Br | Br | CH₂CH₃ | C(CH₃)₃ |
| 146 | Br | Br | CH(CH₃)₂ | C(CH₃)₃ |
| 147 | Br | Br | C(CH₃)₃ | C(CH₃)₃ |
| 148 | I | I | CH₂CH(CH₃)₂ | CH₃ |
| 149 | I | I | CH₂CH(CH₃)₂ | CH₂CH₃ |
| 150 | I | I | CH₂CH(CH₃)₂ | CH(CH₃)₂ |
| 151 | I | I | CH₃ | CH₂CH(CH₃)₂ |
| 152 | I | I | CH₂CH₃ | CH₂CH(CH₃)₂ |
| 153 | I | I | CH(CH₃)₂ | CH₂CH(CH₃)₂ |
| 154 | I | I | CH₂CH(CH₃)₂ | CH₂CH(CH₃)₂ |
| 155 | I | I | CH₂C(CH₃)₃ | CH₃ |
| 156 | I | I | CH₂C(CH₃)₃ | CH₂CH₃ |
| 157 | I | I | CH₂C(CH₃)₃ | CH(CH₃)₂ |
| 158 | I | I | CH₂C(CH₃)₃ | C(CH₃)₃ |
| 159 | I | I | CH₃ | CH₂C(CH₃)₃ |
| 160 | I | I | CH₂CH₃ | CH₂C(CH₃)₃ |
| 161 | I | I | CH(CH₃)₂ | CH₂C(CH₃)₃ |

TABLE IB-continued

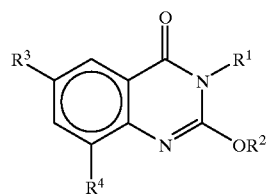

| Compound No. | R³ | R⁴ | R¹ | R² |
|---|---|---|---|---|
| 162 | I | I | C(CH₃)₃ | CH₂C(CH₃)₃ |
| 163 | Br | Br | CH₂CH(CH₃)₂ | CH₃ |
| 164 | Br | Br | CH₂CH(CH₃)₂ | CH₂CH₃ |
| 165 | Br | Br | CH₂CH(CH₃)₂ | CH(CH₃)₂ |
| 166 | Br | Br | CH₃ | CH₂CH(CH₃)₂ |
| 167 | Br | Br | CH₂CH₃ | CH₂CH(CH₃)₂ |
| 168 | Br | Br | CH(CH₃)₂ | CH₂CH(CH₃)₂ |
| 169 | Br | Br | CH₂CH(CH₃)₂ | CH₂CH(CH₃)₂ |
| 170 | Br | Br | CH₂C(CH₃)₃ | CH₃ |
| 171 | Br | Br | CH₂C(CH₃)₃ | CH₂CH₃ |
| 172 | Br | Br | CH₂C(CH₃)₃ | CH(CH₃)₂ |
| 173 | Br | Br | CH₂C(CH₃)₃ | C(CH₃)₃ |
| 174 | Br | Br | CH₃ | CH₂C(CH₃)₃ |
| 175 | Br | Br | CH₂CH₃ | CH₂C(CH₃)₃ |
| 176 | Br | Br | CH(CH₃)₂ | CH₂C(CH₃)₃ |
| 177 | Br | Br | C(CH₃)₃ | CH₂C(CH₃)₃ |
| 178 | I | I | CH₂CH(cyclopropyl) | CH₃ |
| 179 | I | I | CH₂CH(cyclopropyl) | CH₂CH₃ |
| 180 | I | I | CH₂CH(cyclopropyl) | CH₂CH₂CH₃ |
| 181 | I | I | CH₃ | CH₂CH(cyclopropyl) |
| 182 | I | I | CH₂CH₃ | CH₂CH(cyclopropyl) |
| 183 | I | I | CH₂CH₂CH₃ | CH₂CH(cyclopropyl) |
| 184 | I | I | cyclobutyl | CH₃ |
| 185 | I | I | cyclobutyl | CH₂CH₃ |
| 186 | I | I | cyclobutyl | CH₂CH₂CH₃ |
| 187 | I | I | CH₃ | cyclobutyl |
| 188 | I | I | CH₂CH₃ | cyclobutyl |
| 189 | I | I | CH₂CH₂CH₃ | cyclobutyl |
| 190 | I | I | cyclopentyl | CH₃ |
| 191 | I | I | cyclopentyl | CH₂CH₃ |
| 192 | I | I | cyclopentyl | CH₂CH₂CH₃ |
| 193 | I | I | CH₃ | cyclopentyl |
| 194 | I | I | CH₂CH₃ | cyclopentyl |
| 195 | I | I | CH₂CH₂CH₃ | cyclopentyl |

TABLE IC

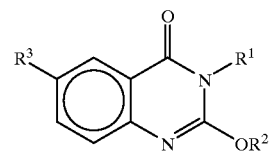

| Compound No. | R³ | R¹ | R² |
|---|---|---|---|
| 196 | I | CH₃ | CH=CH₂ |
| 197 | I | CH₂CH₃ | CH=CH₂ |
| 198 | I | CH₂CH₂CH₃ | CH=CH₂ |
| 199 | I | CH₃ | CH₂CH=CH₂ |

TABLE IC-continued

| Compound No. | R³ | R¹ | R² |
|---|---|---|---|
| 200 | I | CH₂CH₃ | CH₂CH=CH₂ |
| 201 | I | CH₂CH₂CH₃ | CH₂CH=CH₂ |
| 202 | I | CH=CH₂ | CH₃ |
| 203 | I | CH₂CH=CH₂ | CH₃ |
| 204 | I | CH=CH₂ | CH₂CH₃ |
| 205 | I | CH₂CH=CH₂ | CH₂CH₃ |
| 206 | I | CH=CH₂ | CH₂CH₂CH₃ |
| 207 | I | CH₂CH=CH₂ | CH₂CH₂CH₃ |
| 208 | I | CH=CH₂ | CH=CH₂ |
| 209 | I | CH=CH₂ | CH₂CH=CH₂ |
| 210 | I | CH₂CH=CH₂ | CH=CH₂ |
| 211 | I | CH₂CH=CH₂ | CH₂CH=CH₂ |
| 212 | Br | CH₃ | CH=CH₂ |
| 213 | Br | CH₂CH₃ | CH=CH₂ |
| 214 | Br | CH₂CH₂CH₃ | CH=CH₂ |
| 215 | Br | CH₃ | CH₂CH=CH₂ |
| 216 | Br | CH₂CH₃ | CH₂CH=CH₂ |
| 217 | Br | CH₂CH₂CH₃ | CH₂CH=CH₂ |
| 218 | Br | CH=CH₂ | CH₃ |
| 219 | Br | CH₂CH=CH₂ | CH₃ |
| 220 | Br | CH=CH₂ | CH₂CH₃ |
| 221 | Br | CH₂CH=CH₂ | CH₂CH₃ |
| 222 | Br | CH=CH₂ | CH₂CH₂CH₃ |
| 223 | Br | CH₂CH=CH₂ | CH₂CH₂CH₃ |
| 224 | Br | CH=CH₂ | CH=CH₂ |
| 225 | Br | CH=CH₂ | CH₂CH=CH₂ |
| 226 | Br | CH₂CH=CH₂ | CH=CH₂ |
| 227 | Br | CH₂CH=CH₂ | CH₂CH=CH₂ |

TABLE ID

| Compound No. | R³ | R⁴ | R¹ | R² |
|---|---|---|---|---|
| 228 | I | I | CH₃ | CH=CH₂ |
| 229 | I | I | CH₂CH₃ | CH=CH₂ |
| 230 | I | I | CH₂CH₂CH₃ | CH=CH₂ |
| 231 | I | I | CH₃ | CH₂CH=CH₂ |
| 232 | I | I | CH₂CH₃ | CH₂CH=CH₂ |
| 233 | I | I | CH₂CH₂CH₃ | CH₂CH=CH₂ |
| 234 | I | I | CH=CH₂ | CH₃ |
| 235 | I | I | CH₂CH=CH₂ | CH₃ |
| 236 | I | I | CH=CH₂ | CH₂CH₃ |
| 237 | I | I | CH₂CH=CH₂ | CH₂CH₃ |
| 238 | I | I | CH=CH₂ | CH₂CH₂CH₃ |
| 239 | I | I | CH₂CH=CH₂ | CH₂CH₂CH₃ |
| 240 | I | I | CH=CH₂ | CH=CH₂ |
| 241 | I | I | CH=CH₂ | CH₂CH=CH₂ |
| 242 | I | I | CH₂CH=CH₂ | CH=CH₂ |
| 243 | I | I | CH₂CH=CH₂ | CH₂CH=CH₂ |
| 244 | Br | Br | CH₃ | CH=CH₂ |
| 245 | Br | Br | CH₂CH₃ | CH=CH₂ |
| 246 | Br | Br | CH₂CH₂CH₃ | CH=CH₂ |
| 247 | Br | Br | CH₃ | CH₂CH=CH₂ |
| 248 | Br | Br | CH₂CH₃ | CH₂CH=CH₂ |

TABLE ID-continued

| Compound No. | R³ | R⁴ | R¹ | R² |
|---|---|---|---|---|
| 249 | Br | Br | CH₂CH₂CH₃ | CH₂CH=CH₂ |
| 250 | Br | Br | CH=CH₂ | CH₃ |
| 251 | Br | Br | CH₂CH=CH₂ | CH₃ |
| 252 | Br | Br | CH=CH₂ | CH₂CH₃ |
| 253 | Br | Br | CH₂CH=CH₂ | CH₂CH₃ |
| 254 | Br | Br | CH=CH₂ | CH₂CH₂CH₃ |
| 255 | Br | Br | CH₂CH=CH₂ | CH₂CH₂CH₃ |
| 256 | Br | Br | CH=CH₂ | CH=CH₂ |
| 257 | Br | Br | CH=CH₂ | CH₂CH=CH₂ |
| 258 | Br | Br | CH₂CH=CH₂ | CH=CH₂ |
| 259 | Br | Br | CH₂CH=CH₂ | CH₂CH=CH₂ |
| 260 | I | Br | CH₃ | CH₂CH=CH₂ |
| 261 | Br | I | CH₃ | CH₂CH=CH₂ |

TABLE II

| Compound No. | R¹ | X | m.p. °C. |
|---|---|---|---|
| 262 | CH₃ | Cl | |
| 263 | (CH₃)₂CH | OH | |
| 264 | (CH₂)₉CH₃ | Cl | |
| 265 | CH₃ | SH | 303–305 |
| 266 | CH₂CH=CH₂ | Cl | |
| 267 | CH₃CH₂ | SH | >210 |
| 268 | (CH₂)₈CH=CH₂ | Cl | |
| 269 | CH₃CH₂CH₂ | SH | |
| 270 | CH₂C≡CH | Cl | |
| 271 | (CH₃)₂CH | SH | |
| 272 | (CH₂)₈C≡CH | Cl | |
| 273 | CH₂\_CH₂/CHCH₂ | OH | 261–264 |
| 274 | CH₂\_CH₂/CHCH₂ | Cl | |
| 275 | CH₂\_CH₂/CHCH₂ | SH | |
| 276 | CH₂\_CH₂/CH(CH₂)₇ | Cl | |
| 277 | (CH₂)₂\_CH₂/CHCH₂ | Cl | |

TABLE II-continued

Structure: 6-iodo-quinazolin-4(3H)-one with R¹ on N3 and X on C2

| Compound No. | R¹ | X | m.p. °C. |
|---|---|---|---|
| 278 | (CH₃)(CH₂CH₂)CHCH | Cl | |
| 279 | (CH₂)₃(CH₂)CHCH₂ (cyclobutylmethyl) | Cl | |
| 280 | CH₃CH₂CH₂ | Cl | 98–100 |
| 281 | (CH₂)₄(CH₂)CHCH₂ (cyclopentylmethyl) | Cl | |
| 282 | CH₃CH₂ | Cl | |
| 283 | (CH₂)₇(CH₂)CHCH₂ (cyclooctylmethyl) | Cl | |
| 284 | (CH₃C | Cl | |
| 285 | (CH₂)₂C(Cl)(Cl)CHCH₂ (2,2-dichlorocyclopropylmethyl) | Cl | |
| 286 | (CH₃)₂CH | Cl | |
| 287 | (CH₂)₂C(F)(F)CHCH₂ (2,2-difluorocyclopropylmethyl) | Cl | |
| 288 | CH₃ | OH | |
| 289 | CH₃(CH₂)₃CH₂ | Cl | |
| 290 | CH₃CH₂ | OH | |
| 291 | CH₃(CH₂)₃CH₂ | OH | |
| 292 | CH₃CH₂CH₂ | OH | >220 |

TABLE III

Structure: 6,8-diiodo-quinazolin-4(3H)-one with R¹ on N3 and X on C2

| Compound No. | R¹ | X | m.p. °C. |
|---|---|---|---|
| 293 | CH₃ | Cl | |
| 294 | (CH₃)₂CH | OH | |
| 295 | (CH₂)₉CH₃ | Cl | |
| 296 | CH₃ | SH | |
| 297 | CH₂CH=CH₂ | Cl | |
| 298 | CH₃CH₂ | SH | |
| 299 | (CH₂)₈CH=CH₂ | Cl | |
| 300 | CH₃CH₂CH₂ | SH | |
| 301 | CH₂C≡CH | Cl | |
| 302 | (CH₃)₂CH | SH | |
| 303 | (CH₂)₈C≡CH | Cl | |
| 304 | cyclopropylmethyl | OH | 235–237 |
| 305 | (CH₂)₂(CH₂)CH(CH₂)₇ | Cl | |
| 306 | cyclopropylmethyl | SH | |
| 307 | (CH₂)₂(CH₂)CH(CH₂)₇ | Cl | |
| 308 | (CH₂)₂(CH₂)CHCH₂ (cyclobutylmethyl) | Cl | |
| 309 | (CH₃)(CH₂CH₂)CHCH | Cl | |
| 310 | (CH₂)₃(CH₂)CHCH₂ (cyclobutylmethyl) | Cl | |
| 311 | CH₃CH₂CH₂ | Cl | 170–173 |
| 312 | (CH₂)₄(CH₂)CHCH₂ (cyclopentylmethyl) | Cl | |
| 313 | CH₃CH₂ | Cl | |
| 314 | (CH₂)₇(CH₂)CHCH₂ (cyclooctylmethyl) | Cl | |
| 315 | (CH₃C | Cl | |
| 316 | (CH₂)₂C(Cl)(Cl)CHCH₂ (2,2-dichlorocyclopropylmethyl) | Cl | |
| 317 | (CH₃)₂CH | Cl | |

TABLE III-continued

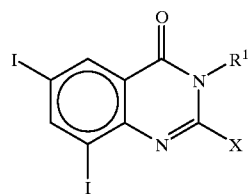

| Compound No. | R¹ | X | m.p. ° C. |
|---|---|---|---|
| 318 | (CH₂)₂C(F)(F)CHCH₂ (cyclic) | Cl | |
| 319 | CH₃ | OH | |
| 320 | CH₃(CH₂)₃CH₂ | Cl | |
| 321 | CH₃CH₂ | OH | |
| 322 | CH₃(CH₂)₃CH₂ | OH | |
| 323 | CH₃CH₂CH₂ | OH | >230 |

TABLE IV

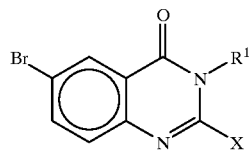

| Compound No. | R¹ | X | m.p. ° C. |
|---|---|---|---|
| 324 | CH₃ | Cl | |
| 325 | (CH₃)₂CH | OH | |
| 326 | (CH₂)₉CH₃ | Cl | |
| 327 | CH₃ | SH | 279–284 |
| 328 | CH₂CH=CH₂ | Cl | 79–81 |
| 329 | CH₃CH₂ | SH | 238–240 |
| 330 | (CH₂)₈CH=CH₂ | Cl | |
| 331 | CH₃CH₂CH₂ | SH | |
| 332 | CH₂C≡CH | Cl | |
| 333 | (CH₃)₂CH | SH | |
| 334 | (CH₂)₈C≡CH | Cl | |
| 335 | cyclopropyl-CH₂ | CH | |
| 336 | cyclopropyl-CH₂ | Cl | |
| 337 | cyclopropyl-CH₂ | SH | 260–266 |
| 338 | cyclopropyl-CH(CH₂)₇ | Cl | |
| 339 | (CH₂)₂CH₂-CHCH₂ (cyclic) | Cl | |

TABLE IV-continued

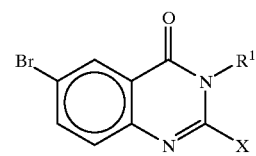

| Compound No. | R¹ | X | m.p. ° C. |
|---|---|---|---|
| 340 | cyclopropyl-CH(CH₃) | Cl | |
| 341 | (CH₂)₃CH₂-CHCH₂ (cyclic) | Cl | |
| 342 | CH₃CH₂CH₂ | Cl | 110–116 |
| 343 | (CH₂)₄CH₂-CHCH₂ (cyclic) | Cl | |
| 344 | CH₃CH₂ | Cl | |
| 345 | (CH₂)₇CH₂-CHCH₂ (cyclic) | Cl | |
| 346 | (CH₃)₃C | Cl | |
| 347 | (CH₂)₂C(Cl)(Cl)CHCH₂ (cyclic) | Cl | |
| 348 | (CH₃)₂CH | Cl | |
| 349 | (CH₂)₂C(F)(F)CHCH₂ (cyclic) | Cl | |
| 350 | CH₃ | OH | |
| 351 | CH₃(CH₂)₂CH₂ | Cl | |
| 352 | CH₃CH₂ | OH | |
| 353 | CH₃(CH₂)₃CH₂ | OH | |
| 354 | CH₃CH₂CH₂ | OH | >210 |
| 355 | CHCH₃)CH₂CH₃ | SH | 183–185 |
| 356 | (CH₂)₄CH₃ | SH | 203–207 |
| 357 | CH₂CH(CH₃)₂ | SH | 243–247 |
| 358 | (CH₂)₃CH₃ | SH | 246–248 |
| 359 | CH₂CH(CH₃)₂ | OH | 250–253 |

TABLE V

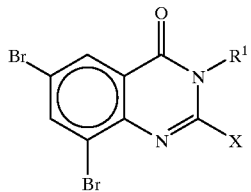

| Compound No. | R¹ | X | m.p. ° C. |
|---|---|---|---|
| 360 | $CH_3$ | Cl | |
| 361 | $(CH_3)_2CH$ | OH | |
| 362 | $(CH_2)_9CH_3$ | Cl | |
| 363 | $CH_3$ | SH | |
| 364 | $CH_2CH=CH_2$ | Cl | |
| 365 | $CH_3CH_2$ | SH | |
| 366 | $(CH_2)_8CH=CH_2$ | Cl | |
| 367 | $CH_3CH_2CH_2$ | SH | |
| 368 | $CH_2C\equiv CH$ | Cl | |
| 369 | $(CH_3)_2CH$ | SH | |
| 370 | $(CH_2)_8C\equiv CH$ | Cl | |
| 371 | $\begin{matrix}CH_2\\|\\CH_2\end{matrix}\!\!>\!CHCH_2$ | OH | |
| 372 | $\begin{matrix}CH_2\\|\\CH_2\end{matrix}\!\!>\!CHCH_2$ | Cl | |
| 373 | $\begin{matrix}CH_2\\|\\CH_2\end{matrix}\!\!>\!CHCH_2$ | SH | |
| 374 | $\begin{matrix}CH_2\\|\\CH_2\end{matrix}\!\!>\!CH(CH_2)_7$ | Cl | |
| 375 | $\begin{matrix}(CH_2)_2\\ \\CH_2\end{matrix}\!\!>\!CHCH_2$ | Cl | |
| 376 | $\begin{matrix}CH_2\;\;\;\;CH_3\\|\;\;\;\;\;\;\;\;\;\;\\CH_2\end{matrix}\!\!>\!CHCH$ | Cl | |
| 377 | $\begin{matrix}(CH_2)_3\\ \\CH_2\end{matrix}\!\!>\!CHCH_2$ | Cl | |
| 378 | $CH_3CH_2CH_2$ | Cl | |
| 379 | $\begin{matrix}(CH_2)_4\\ \\CH_2\end{matrix}\!\!>\!CHCH_2$ | Cl | |
| 380 | $CH_3CH_2$ | Cl | |
| 381 | $\begin{matrix}(CH_2)_7\\ \\CH_2\end{matrix}\!\!>\!CHCH_2$ | Cl | |
| 382 | $(CH)_3C$ | Cl | |

TABLE V-continued

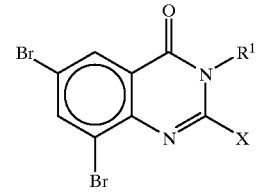

| Compound No. | R¹ | X | m.p. ° C. |
|---|---|---|---|
| 383 | $\begin{matrix}(CH_2)\\|\\C\\/\;\;\backslash\\Cl\;\;\;Cl\end{matrix}\!\!>\!CHCH_2$ | Cl | |
| 384 | $(CH_3)_2CH$ | Cl | |
| 385 | $\begin{matrix}(CH_2)\\|\\C\\/\;\;\backslash\\F\;\;\;F\end{matrix}\!\!>\!CHCH_2$ | Cl | |
| 387 | $CH_3(CH_2)_3CH_2$ | Cl | |
| 388 | $CH_3CH_2$ | OH | |
| 389 | $CH_3(CH_2)_3CH_2$ | OH | |
| 390 | $CH_3CH_2CH_2$ | OH | |

What is claimed:
1. A process for preparing a quinazolinone of Formula I

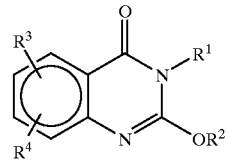

wherein
R¹ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; or $C_3$–$C_{10}$ alkynyl;
R² is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; $C_4$–$C_{10}$ cycloalkyl; $C_4$–$C_{10}$ halocycloalkyl; or $C_3$–$C_{10}$ alkynyl; and R³ and R⁴ are each independently hydrogen or halogen;
characterized by employing a process sequence comprising:
(a) treating a 2-thioquinazolinedione of Formula IIa

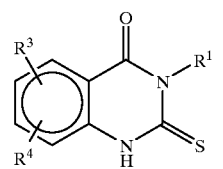

with phosgene in an inert solvent, at a temperature of from about 50 to 1 20° C., and a pressure of from about 1 to 5 atmospheres, to form a 2-chloro-4(3H)-quinazolinone of Formula IIb

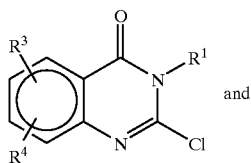

(b) treating the 2-chloro-4(3H)-quinazolinone with a metal alkoxide of Formula M$^+$($^-$OR 2) wherein M is lithium, sodium or potassium, in an inert solvent, at a temperature of from about −20 to 50° C., and a pressure from about 1 to 5 atmospheres.

2. The process of claim 1 wherein the 2-thioquinazolinedione is treated in (a) with phosgene in a solvent selected from inert ester solvents and inert aromatic solvents.

3. The process of claim 1 wherein $R^1$ is $C_1$–$C_3$ alkyl, $R^2$ is $C_1$–$C_3$ alkyl, $R^3$ is Br or, and $R^4$ is H, Br or I.

4. The process of claim 3 wherein (a) 2,3-dihydro-6-iodo-3-propyl-2-thioxo-4(1H)-quinazolinone is reacted with phosgene to give 2-chloro-6-iodo-3-propyl-4(3H)-quinazolinone ; and (b) the 2-chloro-6-iodo-3-propyl-4(3H)-quinazolinone is treated with sodium propoxide or potassium propoxide to prepare 6-iodo-2-propoxy-3-propyl-4(3H)-quinazolinone.

5. A process for preparing a quinazolinone of Formula I

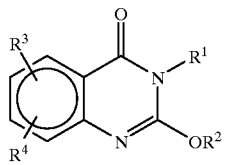

wherein:

$R^1$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; or $C_3$–$C_{10}$ alkynyl;

$R^2$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; $C_4$–$C_{10}$ cycloalkyl; $C_4$–$C_{10}$ halocycloalkyl; or $C_3$–$C_{10}$ alkynyl; and $R^3$ and $R^4$ are each independently hydrogen or halogen;

characterized by employing a process sequence comprising:

treating an anthranilic acid or ester of Formula 1b

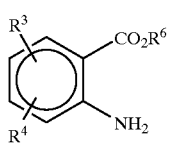

wherein $R^6$ is hydrogen or $C_1$–$C_6$ alkyl with a compound of Formula III

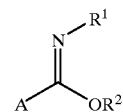

wherein A is Cl or S($C_1$–$C_6$ alkyl) optionally in the presence of an acid or a base, and an inert solvent at a temperature of from about 0 to 100° C., and a pressure of from about 1 to 5 atmospheres.

6. The process of claim 5 wherein $R^1$ is $C_1$–$C_3$ alkyl, $R^2$ is $C_1$–$C_3$ alkyl, $R^3$ is Br or I, and $R^4$ is H, Br or I.

7. The process of claim 6 wherein 2-amino-5-iodobenzoic acid is treated with S-methyl, O-propyl-propylcarbonimidothioate.

8. A process for preparing a quinazolinone of Formula I

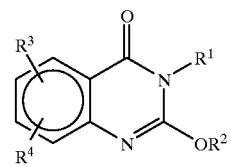

wherein $R^1$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; or $C_3$–$C_{10}$ alkynyl;

$R^2$ is $C_1$–$C_{10}$ alkyl; $C_3$–$C_{10}$ alkenyl; $C_3$–$C_{10}$ cycloalkyl; $C_3$–$C_{10}$ halocycloalkyl; $C_4$–$C_{10}$ cycloalkylalkyl; $C_4$–$C_{10}$ halocycloalkylalkyl; $C_4$–$C_{10}$ cycloalkyl; $C_4$–$C_{10}$ halocycloalkyl; or $C_3$–$C_{10}$ alkynyl; and $R^3$ and $R^4$ are each independently hydrogen or halogen;

characterized by employing a process sequence comprising:

(a) treating an anthranilate ester of Formula 1c

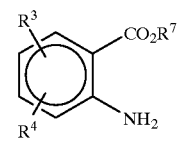

wherein $R^7$ is $C_1$–$C_6$ alkyl with carbon disulfide in an inert solvent at a temperature of from about 25 to 150° C. and a pressure of from about 1 to 5 atmospheres to form an isothiocyanate ester of Formula IV

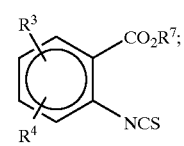

(b) treating the isothiocyanate ester with an alcohol of the formula $R^2$OH in an inert solvent at a temperature of from about 25 to 150° C. and a pressure from about 1 to 5 atmospheres to form a thionocarbamate of Formula 4

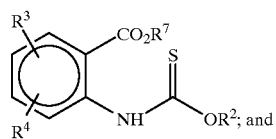

(c) treating the thionocarbamate of Formula 4 with an amine of the formula $R^1$—$NH_2$ in the presence of an inert solvent, at a temperature of from about 25° to 200° C., and a pressure of from about 1 to 5 atmospheres.

9. The process of claim 8 wherein the anthranilate ester of Formula Ic is treated in a heterogeneous system comprising an inert hydrocarbon solvent and aqueous base.

10. A process of claim 8 wherein $R^1$ is $C_1$–$C_3$ alkyl $R^2$ is $C_1$–$C_3$ alkyl $R^3$ is Br or and $R^4$ is H, Br or I.

11. The process of claim 10 wherein (a) methyl 2-amino-5-iodobenzoate is treated to form methyl 5-iodo-2-isothiocyanatobenzoate; (b) the methyl 5-iodo-2-isothiocyanatobenzoate is treated with n-propanol to form methyl 5-iodo-2((propoxy-thioxomethyl)-amino)benzoate, and (c) the methyl 5-iodo-2-((propoxythioxomethyl)-amino) benzoate is treated with propylamine.

12. The process of claim 8 wherein the anthranilate ester of Formula 1c is treated in a heterogeneous system comprising toluene or xylene.

* * * * *